(12) United States Patent
Aurongzeb et al.

(10) Patent No.: US 11,590,411 B2
(45) Date of Patent: Feb. 28, 2023

(54) PRESSURE SENSOR WITH MICROPHONE AND METAL OXIDE SENSOR OF A GAMING HEADSET MICROPHONE MOUTHPIECE

(71) Applicant: Dell Products, LP, Round Rock, TX (US)

(72) Inventors: Deeder M. Aurongzeb, Austin, TX (US); Peng Lip Goh, Singapore (SG)

(73) Assignee: Dell Products, LP, Round Rock, TX (US)

( * ) Notice: Subject to any disclaimer, the term of this patent is extended or adjusted under 35 U.S.C. 154(b) by 295 days.

(21) Appl. No.: 17/125,762

(22) Filed: Dec. 17, 2020

(65) Prior Publication Data
US 2022/0193536 A1    Jun. 23, 2022

(51) Int. Cl.
| | | |
|---|---|---|
| *A63F 13/00* | (2014.01) | |
| *A63F 9/24* | (2006.01) | |
| *A63F 13/212* | (2014.01) | |
| *H04R 1/10* | (2006.01) | |
| *A61B 5/08* | (2006.01) | |
| *A63F 13/218* | (2014.01) | |
| *A63F 13/215* | (2014.01) | |
| *A61B 5/083* | (2006.01) | |

(52) U.S. Cl.
CPC .......... *A63F 13/212* (2014.09); *A61B 5/0816* (2013.01); *A61B 5/0836* (2013.01); *A63F 13/215* (2014.09); *A63F 13/218* (2014.09); *H04R 1/1091* (2013.01); *A61B 2562/028* (2013.01); *A61B 2562/0247* (2013.01)

(58) Field of Classification Search
CPC .... A63F 13/212; A63F 13/215; A63F 13/218; A61B 5/0816; A61B 5/0836; A61B 2562/0247; A61B 2562/028; H04R 1/1091
See application file for complete search history.

(56) References Cited

U.S. PATENT DOCUMENTS 5,610,674 A * 3/1997 Martin ................. B01F 23/215
352/85
10,365,716 B2    7/2019 Aimone
(Continued)

FOREIGN PATENT DOCUMENTS

WO    2016/074042 A1    5/2016

*Primary Examiner* — Milap Shah
*Assistant Examiner* — Jason Pinheiro
(74) *Attorney, Agent, or Firm* — Prol Intellectual Property Law, PLLC; H. Kenneth Prol

(57) ABSTRACT

A biofeedback headset for providing input to and receiving output from an information handling system may include a controller to send and receive audio signals to and from the information handling system and send biofeedback signals to the information handling system; one or more speakers mounted to a wearable head band to provide audio output from the information handling system to a user; and a mouthpiece operatively coupled to the wearable headband including: a microphone to receive audio input from the user; a pressure sensor to detect a breathing rate and amplitude of the user and, with the controller, provide breathing rate and amplitude biofeedback signals to the information handling system; and a gas sensor to detect a composition of air at the mouthpiece as the user respirates and, with the controller, provide air composition biofeedback signals to the information handling system.

20 Claims, 11 Drawing Sheets

(56) References Cited

U.S. PATENT DOCUMENTS

| | | |
|---|---|---|
| 10,606,353 B2 | 3/2020 | Ce Coleman |
| 10,768,665 B2 | 9/2020 | Aimone |
| 10,775,894 B2 | 9/2020 | Maalouf |
| 11,128,636 B1* | 9/2021 | Jorasch .................... G06F 3/015 |
| 2008/0146892 A1* | 6/2008 | LeBoeuf .............. A61B 5/0022 |
| | | 600/300 |
| 2013/0131519 A1* | 5/2013 | LeBoeuf .............. A61B 5/1455 |
| | | 600/476 |
| 2014/0140567 A1* | 5/2014 | LeBoeuf .................. A61B 5/01 |
| | | 381/381 |
| 2014/0225738 A1* | 8/2014 | Lechner ............ H04M 1/72418 |
| | | 340/603 |
| 2015/0199010 A1 | 7/2015 | Coleman |
| 2015/0309316 A1* | 10/2015 | Osterhout ........... G06F 3/03547 |
| | | 345/8 |
| 2016/0199602 A1* | 7/2016 | Fernandez .......... A61M 16/021 |
| | | 128/202.13 |
| 2018/0314321 A1* | 11/2018 | Primus .................... G06F 3/011 |
| 2019/0243454 A1 | 8/2019 | Chia-Chieh Sun |
| 2020/0093459 A1 | 3/2020 | Rahman |
| 2020/0099411 A1* | 3/2020 | Ruttler .................. H04B 1/385 |
| 2020/0151965 A1* | 5/2020 | Forbes .................. G06T 19/006 |
| 2020/0261009 A1 | 8/2020 | Everman |
| 2020/0289922 A1* | 9/2020 | McCoy .................. A63F 13/428 |
| 2021/0399911 A1* | 12/2021 | Jorasch ................. H04L 65/403 |
| 2022/0160044 A1* | 5/2022 | Moubarak .............. A24F 40/65 |

\* cited by examiner

US 11,590,411 B2

PRESSURE SENSOR WITH MICROPHONE AND METAL OXIDE SENSOR OF A GAMING HEADSET MICROPHONE MOUTHPIECE

FIELD OF THE DISCLOSURE

The present disclosure generally relates to input/output devices of a gaming system. The present disclosure more specifically relates to a headset used during game play at an information handling system.

BACKGROUND

As the value and use of information continues to increase, individuals and businesses seek additional ways to process and store information. One option available to clients is information handling systems. An information handling system generally processes, compiles, stores, and/or communicates information or data for business, personal, or other purposes thereby allowing clients to take advantage of the value of the information. Because technology and information handling may vary between different clients or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific client or specific use, such as e-commerce, financial transaction processing, airline reservations, enterprise data storage, or global communications. In addition, information handling systems may include a variety of hardware and software components that may be configured to process, store, and communicate information and may include one or more computer systems, data storage systems, and networking systems. The information handling system may include telecommunication, network communication, and video communication capabilities. Further, the information handling system may include an output and input device used by the user to receive visual and audio output and provide audio and other types of input to the information handling system.

BRIEF DESCRIPTION OF THE DRAWINGS

It will be appreciated that for simplicity and clarity of illustration, elements illustrated in the Figures are not necessarily drawn to scale. For example, the dimensions of some elements may be exaggerated relative to other elements. Embodiments incorporating teachings of the present disclosure are shown and described with respect to the drawings herein, in which.

The use of the same reference symbols in different drawings may indicate similar or identical items.

DETAILED DESCRIPTION OF THE DRAWINGS

Figure 1:
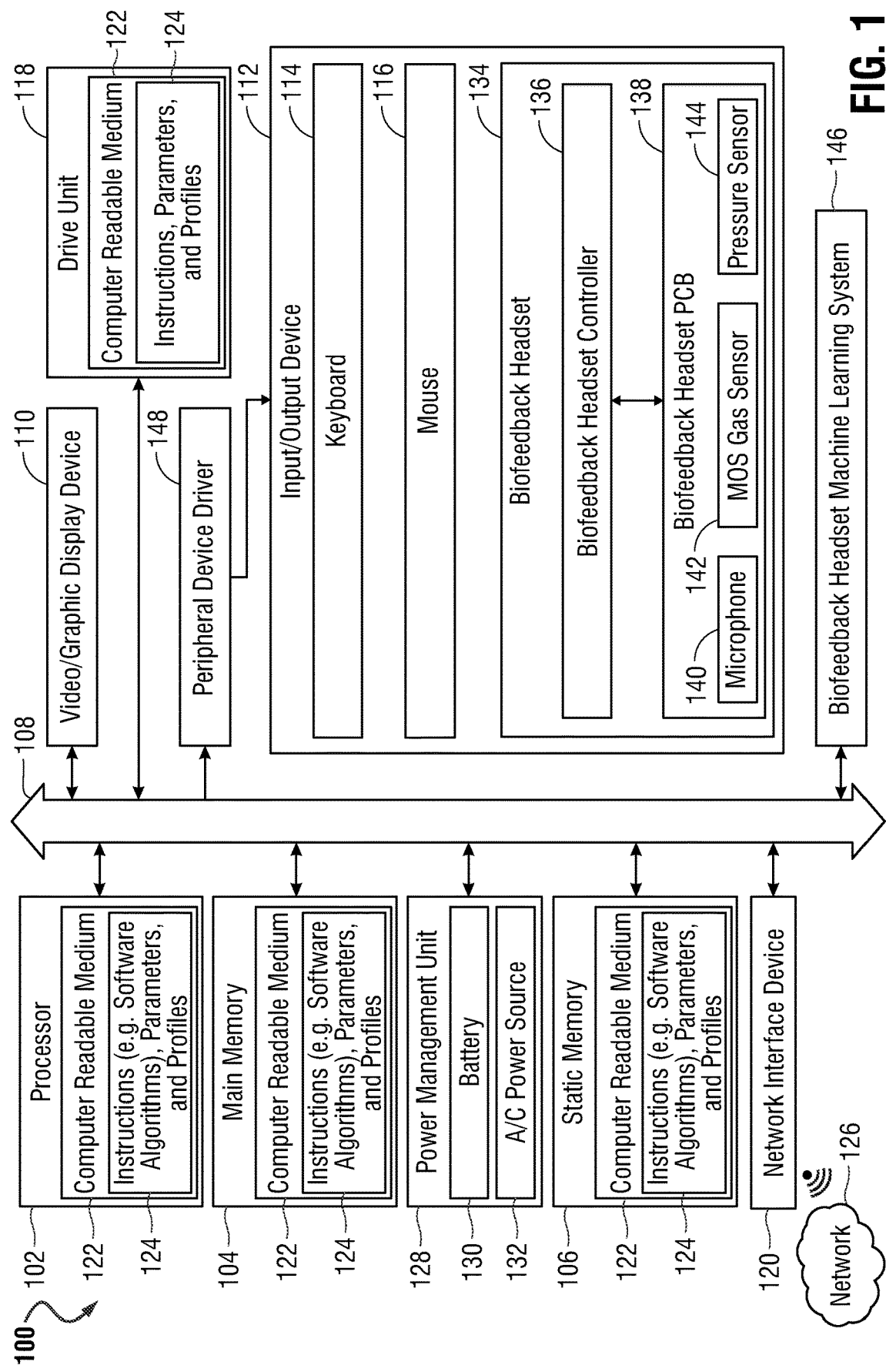
FIG. 1 is a block diagram illustrating an information handling system according to an embodiment of the present disclosure.

The following description in combination with the Figures is provided to assist in understanding the teachings disclosed herein. The description is focused on specific implementations and embodiments of the teachings, and is provided to assist in describing the teachings. This focus should not be interpreted as a limitation on the scope or applicability of the teachings.

The present specification describes a biofeedback headset used to provide biofeedback to the information handling system during use by a user. Information handling systems may include a number of hardware devices as well as software that allows a user to engage in gaming activities. Often these information handling systems include specific hardware that allows for quick execution of computer code in order to generate the graphics and sounds associated with the execution of a gaming application. Often, these graphics may be generated by, for example, a graphics processing unit (GPU) or other processor that presents to the user a view of a gaming environment on a computer screen or others display device. This display device may be one of many output devices that immerses the user into the gaming experience and allows the user to more fully engage in the gaming environment. These input/output devices are used to better immerse the user into the action of the game play as it is presented to the user.

In order to better provide input to the information handling system, the user may also interact with a mouse, a keyboard, or some other input device. Implementation by the user of these specific input devices allows the user to interact with the gaming environment. Another specific type of input device may include a headset. A headset may include, in some embodiments, any number of speakers that provide audio output to a user representative of sounds produced by the execution of the gaming application. Additionally, the headset may include a microphone that receives audio input from the user when the user talks. In any gaming scenario and especially in online cooperative gaming scenarios, this audio input from the user may be provided to other users who are also engaged in the same gaming environment at, for example, remote locations from the first user. The microphone specifically may relay audio data to the other users in order to coordinate actions in the gaming environment during, for example, a multiplayer online gaming environment.

The biofeedback headset described herein may provide for additional gaming features used by the user in order to increase interaction with the execution of the gaming application as well as provide biofeedback to the user related to, in an example, the user's current health and or health concerns resulting from the engagement of game play by the user. In an embodiment, the biofeedback headset described herein includes a pressure sensor (e.g., an air pressure sensor). This pressure sensor may detect a breathing amplitude and breathing rate of the user during game play. This data may also be compared to sounds received at a microphone in the biofeedback headset as well. In an embodiment, the pressure sensor may be a microelectromechanical systems (MEMS) capacitive pressure sensor formed into a mouthpiece of the biofeedback headset. The MEMS capacitive pressure sensor may be fluidically coupled to a micro-fan via a tube such that air may be passed across the pressure sensor at a certain rate in order to get an accurate pressure measurement at any given time as altered by a user's breath near the mouthpiece.

In an embodiment, the biofeedback headset described herein may include a gas sensor. The gas sensor may also be placed on the mouthpiece where the user may respirate onto it. In an embodiment, the gas sensor may be a solid-state sensor device that may detect a composition of air the user respirates such as an amount of $CO_2$ and/or $O_2$ respirated by the user. In an embodiment, the gas sensor may be a microelectromechanical systems (MEMS) metal oxide semiconductor (MOS) gas sensor formed into a mouthpiece of the biofeedback headset. The MEMS MOS gas sensor may be fluidically coupled to the micro-fan via a tube such that air may be passed across the MEMS MOS gas sensor at a certain rate in order to detect any increase in $CO_2$ and/or $O_2$ around the mouthpiece of the biofeedback headset as altered by a user's breathing near the mouthpiece.

The data signals from the MEMS capacitive pressure sensor, microphone, and MEMS MOS gas sensor may be presented to a controller on the biofeedback headset. This controller may relay these data signals, via a wired or wireless connection for example, to a controller executing a biofeedback headset machine learning system. The biofeedback headset machine learning system may be implemented to monitor for potential health issues associated with the user engaged in game play and determine which, if any, health messages are to be provided to a user during this game play.

Embodiments of the present disclosure provides for a biofeedback headset for providing input to and receiving output from an information handling system that includes a controller to send and receive audio signals to and from the information handling system and send biofeedback signals to the information handling system. The biofeedback headset may further include a wired connection to the information handling system including a data line for the controller to send and receive the audio signals and send the biofeedback signals and a power line to provide power to the controller. In an embodiment, the biofeedback headset may further include a mouthpiece operatively coupled to the biofeedback headset that includes a microphone to receive audio input, a pressure sensor to detect a breathing rate and amplitude of the user and, with the controller, provide breathing rate and amplitude biofeedback signals to a biofeedback headset machine learning system of the information handling system, and a gas sensor to detect a composition of air at the mouthpiece as the user respirates and, with the controller, provide air composition biofeedback signals to a biofeedback headset machine learning system of the information handling system.

In an embodiment, the biofeedback headset may include a micro-fan fluidically coupled to the pressure sensor to draw air into the mouthpiece at constant pressure at the pressure sensor. In an embodiment, the biofeedback headset may include a micro-fan fluidically coupled to the gas sensor to pass air respirated by the user over the gas sensor. In an embodiment, the pressure sensor includes a microelectromechanical systems (MEMS) capacitive pressure sensor to detect a change in pressure above a base air pressure. In an embodiment, the gas sensor includes a microelectromechanical systems (MEMS) metal oxide semiconductor (MOS) gas sensor that measures an amount of carbon dioxide ($CO_2$) at the mouthpiece.

In an embodiment, the biofeedback headset may include a first earpiece to house a first speaker for a first ear of the user and a second earpiece to house a second speaker for a second ear of the user. The speakers are used to provide audio output to a user during game play.

The embodiments described herein further describe an information handling system executing a gaming application, including a processor, a memory, a power source, and a biofeedback headset. The biofeedback headset may include a controller to send and receive audio signals to and from the information handling system and send biofeedback signals to the information handling system from a pressure sensor used detect a breathing rate and amplitude of the user; and a gas sensor used to detect a composition of air the user respirates. The biofeedback headset, in an embodiment, also includes a biofeedback headset machine learning system to use, as input, the biofeedback signals from the pressure sensor and gas sensor and provide, as output, health messages to the user determined from the biofeedback inputs via a classification machine learning engine or system.

The present specification further describes a biofeedback headset for providing input to and receiving output from an information handling system that includes a controller to send and receive audio signals to and from the information handling system and send biofeedback signals to the information handling system, a wired connection to the information handling system including a data line for the controller to send and receive the audio signals and send the biofeedback signals and a power line to provide power to the controller. The biofeedback headset further includes a mouthpiece operatively coupled to the biofeedback headset including a microphone to receive audio input, a pressure sensor to detect a breathing rate and amplitude of the user and, with the controller, provide breathing rate and amplitude biofeedback signals to a biofeedback headset machine learning system of the information handling system, and a gas sensor to detect a composition of air at the mouthpiece as the user respirates and, with the controller, provide air composition biofeedback signals to a biofeedback headset machine learning system of the information handling system.

In an embodiment, the biofeedback headset may include a micro-fan to draw air over the pressure sensor and maintain a benchmark pressure at the pressure sensor. In an embodiment, the biofeedback headset may include a rubber-sealed chamber to seal the gas sensor and pressure sensor from a microphone chamber housing the microphone.

In an embodiment, the biofeedback headset may include a micro-fan to draw air over the pressure sensor and gas sensor, a micro-fan tube fluidically coupling the micro-fan to a sensor chamber housing the gas sensor and pressure sensor, and a signal cable placed with the micro-fan tube to send signals from the gas sensor and pressure sensor to the controller. In an embodiment, the biofeedback headset may include a microphone tube operatively coupling the mouthpiece to a portion of a housing of the biofeedback headset to provide an audio soundwave connection to an audio sensor or to provide structural support to a microphone signal cable placed coaxially within the microphone tube and operatively coupling the microphone audio sensor to the controller. The microphone audio sensor may be a solid-state microphone sensor of any type as understood in the art.

FIG. 1 illustrates an information handling system 100 similar to information handling systems according to several aspects of the present disclosure. In the embodiments described herein, an information handling system includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, an information handling system 100 can be a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile information handling system, a palmtop computer, a laptop computer, a desktop computer, a communications device, an access point (AP), a base station transceiver, a wireless telephone, a control system, a camera, a scanner, a facsimile machine, a printer, a pager, a personal trusted device, a web appliance, or any other suitable machine capable of executing a set of instructions (sequential or otherwise) that specify actions to be taken by that machine, and can vary in size, shape, performance, price, and functionality.

In a networked deployment, the information handling system 100 may operate in the capacity of a server or as a client computer in a server-client network environment, or as a peer computer system in a peer-to-peer (or distributed) network environment. In a particular embodiment, the information handling system 100 can be implemented using electronic devices that provide voice, video or data communication. For example, an information handling system 100 may be any mobile or other computing device capable of executing a set of instructions (sequential or otherwise) that specify actions to be taken by that machine. Further, while a single information handling system 100 is illustrated, the term "system" shall also be taken to include any collection of systems or sub-systems that individually or jointly execute a set, or multiple sets, of instructions to perform one or more computer functions.

The information handling system 100 can include memory 104, 106 (volatile (e.g. random-access memory, etc.), nonvolatile (read-only memory, flash memory etc.) or any combination thereof), one or more processing resources, such as a central processing unit (CPU) or a processor 102, a graphics processing unit (GPU), hardware or software control logic, or any combination thereof. Additional components of the information handling system 100 can include one or more storage devices, one or more communications ports for communicating with external devices, as well as, various input and output (I/O) devices 112, such as a keyboard 114, a mouse 116, a video/graphic display 110, or any combination thereof. The information handling system 100 can also include one or more buses 108 operable to transmit communications between the various hardware components. Portions of an information handling system 100 may themselves be considered information handling systems 100.

As described herein, as part of an input/output device 112, the information handling system 100 includes a biofeedback headset 134. The biofeedback headset 134 described herein may be used by a user to provide input to the information handling system 100 in the form of sounds received at a microphone 140 of the biofeedback headset 134. Additional types of input may also be provided to the information handling system 100 through the use of a metal oxide semiconductor (MOS) gas sensor 142 and a pressure sensor 144. In an embodiment, the pressure sensor 144 may measure the rate of breathing by the user as well as the magnitude of breath produced by the user. In an embodiment, the MOS gas sensor 142 may measure the composition of the user breath such as the $CO_2$ or $O_2$ composition of that air. The information handling system 100 may additionally receive this data from the biofeedback headset 134 and, with the execution of a biofeedback headset machine learning system 146, provide physiological feedback, for example, to the user via a warning or status message to the user at the video/graphic display device 110. In an embodiment, the biofeedback headset machine learning system 146 may use, as input, game play interaction of the user during the execution of the gaming application, intensity of the game play during the execution of the gaming application, a difficulty level during the execution of the gaming application, an opponent level difficulty during the execution of the gaming application, and teamwork level during the execution of the gaming application. This input may come from the user engaged with the gaming application or any other user that has engaged with any gaming application. The present disclosure describes in more detail the functionalities of the biofeedback headset 134 and biofeedback headset machine learning system 146 herein.

Information handling system 100 can include devices or modules that embody one or more of the devices or execute instructions for the one or more systems and modules described herein, and operates to perform one or more of the methods described herein. The information handling system 100 may execute code instructions 124 that may operate on servers or systems, remote data centers, or on-box in individual client information handling systems according to various embodiments herein. In some embodiments, it is understood any or all portions of code instructions 124 may operate on a plurality of information handling systems 100.

The information handling system 100 may include a processor 102 such as a central processing unit (CPU), control logic or some combination of the same. Any of the processing resources may operate to execute code that is either firmware or software code. Moreover, the information handling system 100 can include memory such as main memory 104, static memory 106, computer readable medium 122 storing instructions 124 of the biofeedback headset machine learning system 146, peripheral device driver 148, and drive unit 118 (volatile (e.g. random-access memory, etc.), nonvolatile (read-only memory, flash memory etc.) or any combination thereof). The information handling system 100 can also include one or more buses 108 operable to transmit communications between the various hardware components such as any combination of various input and output (I/O) devices.

The information handling system 100 may further include a video display 110. The video display 110 in an embodiment may function as a liquid crystal display (LCD), an organic light emitting diode (OLED), a flat panel display, or a solid-state display. Additionally, the information handling system 100 may include an input/output device 112, such as a cursor control device (e.g., mouse, touchpad, or gesture or touch screen input), a keyboard 114, and the biofeedback headset 134 described herein. The information handling system 100 can also include a disk drive unit 118.

The network interface device 120 can provide connectivity to a network 126, e.g., a wide area network (WAN), a local area network (LAN), wireless local area network (WLAN), a wireless personal area network (WPAN), a wireless wide area network (WWAN), or other networks using, for example, a wireless adapter. Connectivity may be via wired or wireless connection. The network interface device 120 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used. In some aspects of the present disclosure, one network interface device 120 may operate two or more wireless links via a wireless adapter.

A wireless adapter associated with the network interface device 120 may connect to any combination of macro-cellular wireless connections including 2G, 2.5G, 3G, 4G, 5G or the like from one or more service providers. Utilization of radiofrequency communication bands according to several example embodiments of the present disclosure may include bands used with the WLAN standards and WWAN carriers, which may operate in both licensed and unlicensed spectrums. For example, both WLAN and WWAN may use the Unlicensed National Information Infrastructure (U-NII) band which typically operates in the ~5 MHz frequency band such as 802.11 a/h/j/n/ac (e.g., center frequencies between 5.170-5.785 GHz). It is understood that any number of available channels may be available under the 5 GHz shared communication frequency band. WLAN, for example, may also operate at a 2.4 GHz band. WWAN may operate in a number of bands, some of which are proprietary but may include a wireless communication frequency band at approximately 2.5 GHz band for example. In additional examples, WWAN carrier licensed bands may operate at frequency bands of approximately 700 MHz, 800 MHz, 1900 MHz, or 1700/2100 MHz for example as well as the NRFR1, NRFR2, bands, and other known bands. In an embodiment, the network interface device 120 with a wireless adapter may transceive within radio frequencies associated with the 5G New Radio (NR) Frequency Range 1 (FR1) or Frequency Range 2 (FR2), or those associated with 4G LTE and other standards predating the 5G communications standards now emerging. NRFR1 may include radio frequencies below 6 GHz. NRFR2 may include radio frequencies above 6 GHz, made available within the now emerging 5G communications standard. Communications within the WLAN or WWAN may be enabled through the use of either an evolved Node B (eNodeB) executing an evolved packet core of an existing LTE system, or a Next Generation Node B (gNodeB) executing the next generation packet core of the 5G cellular standard.

In some embodiments, software, firmware, dedicated hardware implementations such as application specific integrated circuits, programmable logic arrays and other hardware devices can be constructed to implement one or more of some systems and methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by firmware or software programs executable by a controller or a processor system. Further, in an exemplary, non-limited embodiment, implementations can include distributed processing, component/object distributed processing, and parallel processing. Alternatively, virtual computer system processing can be constructed to implement one or more of the methods or functionality as described herein.

The present disclosure contemplates a computer-readable medium that includes instructions, parameters, and profiles 124 or receives and executes instructions, parameters, and profiles 124 responsive to a propagated signal, so that a device connected to a network 126 can communicate voice, video or data over the network 126. Further, the instructions 124 may be transmitted or received over the network 126 via the network interface device 120 or wireless adapter.

The information handling system 100 can include a set of instructions 124 that can be executed to cause the computer system to perform any one or more of the methods or computer-based functions disclosed herein. For example, instructions 124 may execute a biofeedback headset machine learning system 146, a gaming application, peripheral device driver 148, software agents, or other aspects or components. Various software modules comprising application instructions 124 may be coordinated by an operating system (OS), and/or via an application programming interface (API). An example operating system may include Windows®, Android®, and other OS types. Example APIs may include Win 32, Core Java API, or Android APIs.

The disk drive unit 118, static memory 106, or a memory in the biofeedback headset 134 may include a computer-readable medium 122 in which one or more sets of instructions 124 such as software can be embedded. Similarly, main memory 104 may also contain a computer-readable medium for storage of one or more sets of instructions, parameters, or profiles 124 including an estimated training duration table. The disk drive unit 118 and static memory 106 may also contain space for data storage. Further, the instructions 124 may embody one or more of the methods or logic as described herein. For example, instructions relating to the biofeedback headset machine learning system 146, gaming applications, and peripheral device driver 148 software algorithms, processes, and/or methods may be stored here. In a particular embodiment, the instructions, parameters, and profiles 124 may reside completely, or at least partially, within the main memory 104, the static memory 106, and/or within the disk drive 118 or memory on an I/O device 112 during execution by the processor 102 or other controllers of information handling system 100. As explained, some or all of the biofeedback headset machine learning system 146 may be executed locally or remotely. The main memory 104 and the processor 102 also may include computer-readable media.

Main memory 104 may contain computer-readable medium (not shown), such as RAM in an example embodiment. An example of main memory 104 includes random access memory (RAM) such as static RAM (SRAM), dynamic RAM (DRAM), non-volatile RAM (NV-RAM), or the like, read only memory (ROM), another type of memory, or a combination thereof. Static memory 106 may contain computer-readable medium (not shown), such as NOR or NAND flash memory in some example embodiments. The biofeedback headset machine learning system 146 and peripheral device driver 148 may be stored in static memory 106, or the drive unit 118 on a computer-readable medium 122 such as a flash memory or magnetic disk in an example embodiment. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random-access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The information handling system 100 may also include the biofeedback headset machine learning system 146 that may be operably connected to the bus 108. The biofeedback headset machine learning system 146 computer readable medium 122 may also contain space for data storage. The biofeedback headset machine learning system 146 may, according to the present description, perform tasks related to receiving data as input and providing, as output, indications of a physiological state of a user implementing the biofeedback headset 134.

In an embodiment, the biofeedback headset machine learning system 146 may communicate with the main memory 104, the processor 102, the video display 110, an alpha-numeric input device (e.g., keyboard 114), and the network interface device 120 via bus 108, and several forms of communication may be used, including ACPI, SMBus, a 24 MHZ BFSK-coded transmission channel, or shared memory. Driver software, firmware, controllers and the like may communicate with applications on the information handling system 100.

In other embodiments, dedicated hardware implementations such as application specific integrated circuits, programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

When referred to as a "system", a "device," a "module," a "controller," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a stand-alone device). The system, device, controller, or module can include software, including firmware embedded at a device, such as an Intel® Core class processor, ARM® brand processors, Qualcomm® Snapdragon processors, or other processors and chipsets, or other such device, or software capable of operating a relevant environment of the information handling system. The system, device, controller, or module can also include a combination of the foregoing examples of hardware or software. In an embodiment an information handling system 100 may include an integrated circuit or a board-level product having portions thereof that can also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another can communicate directly or indirectly through one or more intermediaries.

The information handling system 100 may further include a power management unit (PMU) 128 (a.k.a. a power supply unit (PSU)). The PMU 128 may manage the power provided to the components of the information handling system 100 such as the processor 102, a cooling system such as a bank of fans, one or more drive units 118, a graphical processing unit (GPU), the video/graphic display device 110, and other components that may require power when a power button has been actuated by a user. In an embodiment, the PMU 128 may be electrically coupled to the bus 108 to provide this power. The PMU 128 may regulate power from a power source such as a battery 130 or A/C power adapter 132. In an embodiment, the battery 130 may be charged via the A/C power adapter 132 and provide power the to the components of the information handling system 100 when A/C power from the A/C power adapter 132 is removed.

As described herein, the information handling system 100 may include, as an input device, a biofeedback headset 134. This biofeedback headset 134 may be operatively coupled to the information handling system 100 via either a wired or wireless connection. In an embodiment, power may be provided to the biofeedback headset 134 via a wired connection. In another embodiment, power may be provided to the biofeedback headset 134 via a battery source at the biofeedback headset 134 in order to allow for a wireless connection to the information handling system 100.

The biofeedback headset 134 may include a number of sensors that allow the user to provide input to the information handling system 100 and the biofeedback headset machine learning system 146 as described herein. In the context of the embodiments described herein, the operations of the biofeedback headset 134, the information handling system 100, and the biofeedback headset machine learning system 146 may be conducted while the user is engaged in game play. This game play occurs as the processor 102 of the information handling system 100 executes a gaming application. A gaming application may be any type of gaming application including, for example, first person shooter games, action games, adventure games, fighting games, puzzle games, role-playing games, simulation games, sports games, strategy games, racing games, and platform games, among others. It is appreciated that the type of game engaged in by the user may elicit certain stress levels and other physiological effects by the user. For example, the stress levels associated with a first-person shooter game may be vastly different than, for example, a puzzle game. The biofeedback headset 134 may be used to detect or determine when these gaming applications have elicited a physiological effect on the user and provide output to the user describing how to overcome any negative physiological effects.

In an embodiment, the biofeedback headset 134 includes a MOS gas sensor 142. The MOS gas sensor 142 may be formed on a biofeedback headset printed circuit board (PCB) 138 and operatively coupled to a biofeedback headset controller 136 placed within the biofeedback headset 134. In an embodiment, the MOS gas sensor 142 is a gas sensor that includes a microelectromechanical systems (MEMS) metal oxide semiconductor (MOS) gas sensor to measure an amount of carbon dioxide ($CO_2$) at the mouthpiece. In an embodiment, the MOS gas sensor 142 may alternatively or additionally measure the $O_2$ composition of the air around the MOS gas sensor 142. During operation the MOS gas sensor 142 may be placed next to the user's mouth using, for example a mouthpiece. The MOS gas sensor 142, in alternative embodiments, may be any other type of gas sensor such as a catalytic gas sensor, an electromechanical gas sensor, a non-dispersive infrared (NDIR) gas sensor, among others. The present specification contemplates that these other types of gas sensors and those developed in the future may be used to detect the user's breath and atmosphere around the mouthpiece. For ease of description the MOS gas sensor 142 will be described and discussed as a MOS-type gas sensor.

As the MOS gas sensor 142 is operating, the user may respirate causing the respirated air to be sensed the by MOS gas sensor 142. The MOS gas sensor 142 may measure the $CO_2$ and/or $O_2$ levels of the user's respirated breath and send those signals to the biofeedback headset controller 136. It has been understood that certain levels of $CO_2$ could indicate poor health or environment for a user. For example, an excellent rate of $CO_2$ is between 400 and 600 ppm while a mediocre to bad level could range from 1100 to 2100 ppm. The MOS gas sensor 142 may detect whether the user is in good or bad conditions that could affect the user's ability to engage in game play or could dramatically affect the user's health. The present specification further contemplates that other types of gas besides or in addition to $CO_2$ and/or $O_2$ may be detected. Among these other types of gases may be volatile organic compounds (VOCs) such as alcohol or carbon monoxide may be detected for example. The presence of these other gases may indicate to a user that the user is in an unhealthy environment and may need to ventilate the area or leave entirely.

This data may be presented to the processor 102 of the information handling system 100 via either the wired or wireless connection to the information handling system 100. The processor 102 may then execute a biofeedback headset machine learning system 146 and use the data received from the biofeedback headset controller 136 and MOS gas sensor 142 as input to generate, when necessary, any warnings or indications to the user at the video/graphic display device 110 that respiration characteristics need to be changed. Other physiological effects on the user as the user may engage in game play at the information handling system 100 may be presented to the user based on the data retrieved from the MOS gas sensor 142. These other physiological effects are contemplated by the present description. In an embodiment, the biofeedback headset machine learning system 146 may be used to also provide these different and additional warnings related to any changes that the user may have experienced based on the data provided by the biofeedback headset controller 136 and the sensors therein.

In an embodiment, the biofeedback headset 134 may include a pressure sensor 144. The pressure sensor 144 may be formed on the biofeedback headset printed circuit board (PCB) 138 and operatively coupled to a biofeedback headset controller 136 placed within the biofeedback headset 134. In an embodiment, the pressure sensor may include a microelectromechanical systems (MEMS) capacitive pressure sensor. Although the present specification describes the pressure sensor 144 as a MEMS capacitive pressure sensor, this is not meant to limit the specification. In an embodiment, the pressure sensor 144 may be a piezoelectric or piezoresistive-type pressure sensor 144.

In an embodiment, the pressure sensor 144 may be placed within a mouthpiece in order to place the pressure sensor 144 at a location near the user's mouth. This will allow the pressure sensor 144 to detect a change in pressure above a base or threshold air pressure. In an embodiment, the base or threshold air pressure may be maintained through the use of a micro-fan fluidically coupled to the pressure sensor 144 in order to set a base air pressure at the pressure sensor 144. As the user breathes on or near the pressure sensor 144, the air pressure will change and this detected difference in air pressure may be sensed and provided to the biofeedback headset controller 136. The biofeedback headset controller 136 may pass the signals detected by the pressure sensor 144 to the processor 102 and biofeedback headset machine learning system 146 of the information handling system 100. Again, these signals may be used as input to the biofeedback headset machine learning system 146 in order to provide the user with any type of biofeedback warnings or status messages at the video/graphic display device 110.

In an embodiment, the biofeedback headset 134 may include a microphone 140. In an embodiment, the microphone 140 may be placed on a mouthpiece that is placed close to the user's mouth. In this embodiment, the microphone 140 is used to detect the user's voice and convert the audio into signals to be received at the biofeedback headset controller 136. Again, the biofeedback headset controller 136 may send the signals from the microphone 140 to the processor 102 of the information handling system 100. In an embodiment, the signals from the microphone 140 may be provided to the biofeedback headset machine learning system 146 as input.

In an embodiment, this input from the microphone 140 into the biofeedback headset machine learning system 146 may be related to the input from the pressure sensor 144. In this embodiment, the relation of the signals from the microphone 140 and the signals from the pressure sensor 144 may be used to determine a breathing rate of the user as the user engages with the gaming application. The breathing rate of the user may help indicate whether a message is to be presented to a user at the video/graphic display device 110 indicating that the user's breath rate is too slow or too fast. As the user engages with the game play, certain events experienced may cause the user to, for example, hold their breath or breath more repetitively. Each of these physiological changes in the user's breathing pattern may indicate that the user risks, for example, hypoxia or hyperventilation. As these conditions could lead to other, relatively more serious conditions such as anxiety, asthma, lung infections, or heart failure, the user may be provided with certain messages on the video/graphic display device 110 to pace their breathing, for example during or after game play. Additionally, a paced breathing state may increase the user's ability to accomplish goals during game play thereby increasing the ability of the user to be more effective. Because a more regulated breathing rate leads to better attentional and cognitive performances, the user is provided with the messages on the video/graphic display device 110 in order to increase their gaming abilities. Additionally, the messages presented to the user on the video/graphic display device 110 may relax the user and may more effectively engage the user in the game play while increasing the accessibility of any given user to increase their game play efficiency.

As described herein, information handling system 100 may include a biofeedback headset machine learning system 146. The biofeedback headset machine learning system 146 may, in an embodiment, according to the present description, perform tasks related to providing, as output, data descriptive of when and which messages are presented to the user at the video/graphic display device 110.

In an embodiment, the biofeedback headset machine learning system 146 may be trained by receiving, as training input, game play interaction of the user during the execution of the gaming application, intensity of the game play during the execution of the gaming application, a difficulty level during the execution of the gaming application, an opponent level difficulty during the execution of the gaming application, and teamwork level during the execution of the gaming application, the signals received from the MOS gas sensor 142, the signals received from the pressure sensor 144, and the signals received from the microphone 140, among other data related to the execution of the gaming application and use of the biofeedback headset 134 by the user. This input may be referred to herein as input data used to either train the biofeedback headset machine learning system 146 or provide input in real-time in order to receive as output indications of a physiological state of a user implementing the biofeedback headset 134.

In an embodiment, the biofeedback headset machine learning system 146 may be code instructions and may operate with the main memory 104, the processor 102, the video/graphic display device 110, the keyboard 114, and the network interface device 120 via bus 108, and several forms of communication may be used, including ACPI, SMBus, a 24 MHZ BFSK-coded transmission channel, or shared memory. Driver software, firmware, controllers, and the like may communicate with applications on the information handling system 100. During this process and after the biofeedback headset machine learning system 146 has been trained, the processor 102 may receive the output from the biofeedback headset machine learning system 146 that defines the indications of a physiological state of a user implementing the biofeedback headset 134. a trained machine learning classifier of the biofeedback headset machine learning system 146 may take inputs from the biofeedback headset 134, other I/) devices, gaming applications and other sensors and sources to classify health or environmental conditions for a user. Upon receipt of this dataset, the processor 102 may cause these indications to be presented to the user at the video/graphic display device 110. By way of example, the output from the biofeedback headset machine learning system 146 may indicate that the user is breathing to heavily which may result in both adverse health effects as well as poor gaming performance. As a result, the processor 102 may provide a message to appear on the video/graphic display device 110 indicating to the user that the breath rate is too frequent and that the user should slow the rate of breathing. In order for the biofeedback headset machine learning system 146 to provide such indication, the breath rate data from the microphone 140 and pressure sensor 144 as well as the air composition data from the MOS gas sensor 142 may be used as input into the biofeedback headset machine learning system 146 and, based on other factors such as the game play the user is engaged in, may provide an appropriate indicator to the user. This indicator, in an embodiment, may include a message flashed across the screen. In an embodiment, the indicator may be an icon placed within a system tray or other notification area usually placed along a lower edge of the viewable surface of the video/graphic display device 110. In an embodiment, the indicator may be an audio indicator presented to the user via one or more speakers within the biofeedback headset 134. The present specification contemplates that any or all of these examples may be used to indicate a specific biofeedback message to the user during game play. In this manner, a user may be presented with appropriate biofeedback that increases the user's attentional and cognitive performance when the user is engaged in game play. This may allow the user to enjoy the game play as well as allow the user to engage with the game play for a longer duration of time due to the reduced mental and bodily stress exerted on the user.

Figure 2:
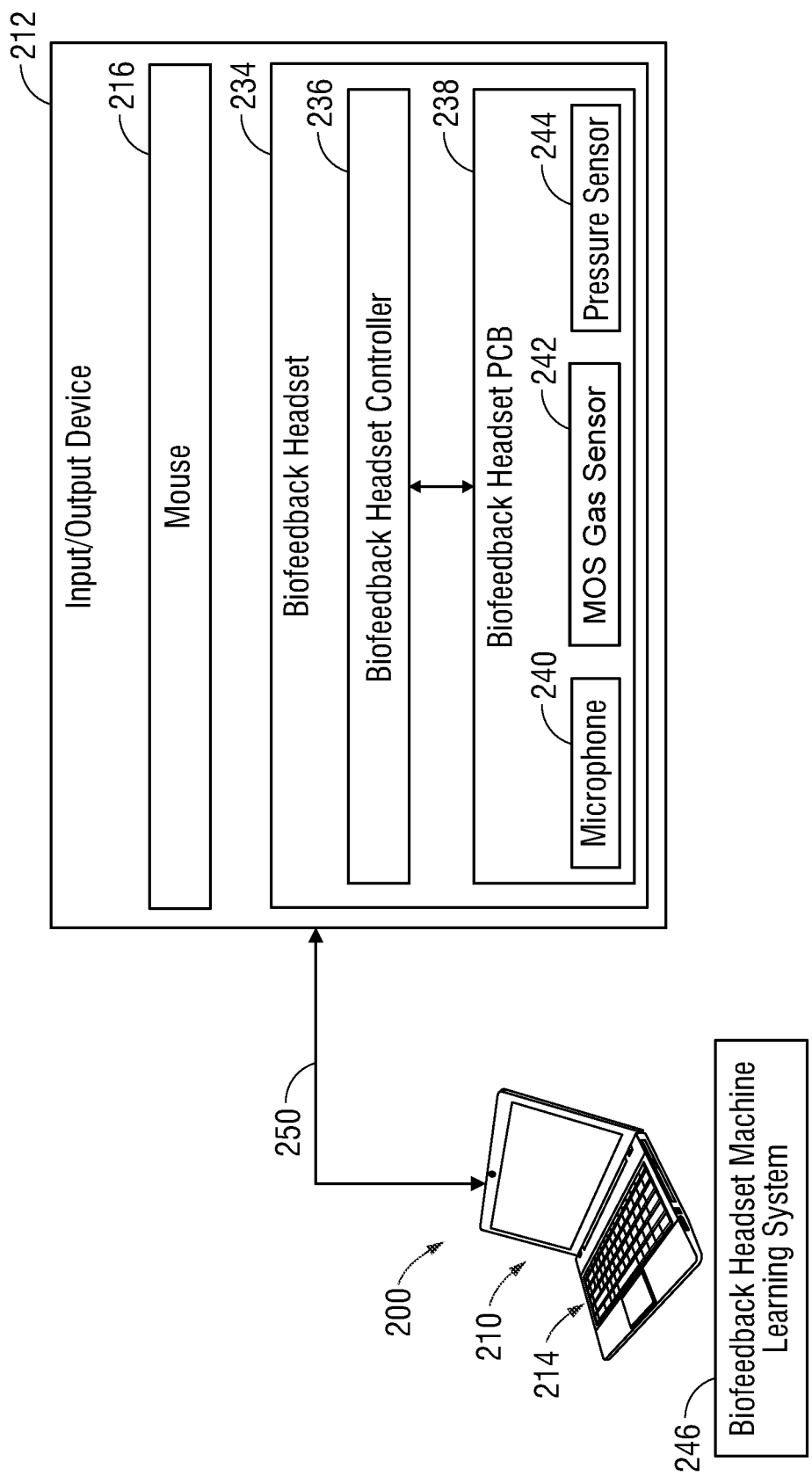
FIG. 2 is a block diagram illustrating an information handling system and a biofeedback headset according to an embodiment of the present disclosure.

FIG. 2 is a block diagram illustrating an information handling system 200 and a biofeedback headset 234 according to an embodiment of the present disclosure. FIG. 2 shows that the biofeedback headset 234 is operatively coupled to the information handling system 200 by a wired or wireless connection 250. Again, the information handling system 200 may include a peripheral device driver (not shown) that interfaces the input/output devices 212 such as a keyboard 214, a mouse 216, and the biofeedback headset 234.

The information handling system 200 includes a video/graphic display device 210 formed, in this example, a display portion of a notebook-type computing device. Additionally, the information handling system 200 may include a keyboard 214 formed into a keyboard portion of that notebook-type information handling system 200. Although FIG. 2 shows the information handling system 200 as being a notebook-type information handling system 200, the present specification contemplates that the information handling system 200 may be any type of information handling system 200 such as a desktop computing system or a tablet-type computing system, among others. In an embodiment, the information handling system 200 may be a desktop gaming system that is customized better to fit a user that is implementing the information handling system 200 to engage in game play as the processor of the information handling system 200 executes a gaming application.

Again, the biofeedback headset 234 may include a number of sensors that allow the user to provide input to the information handling system 200 and the biofeedback headset machine learning system 246 as described herein. In the context of the embodiments described herein, the operations of the biofeedback headset 234, the information handling system 200, and the biofeedback headset machine learning system 246 may be conducted while the user is engaged in game play. In some embodiments, the user engages with a mouse 216 and the biofeedback headset 234 at a remote location from the information handling system 200 with both the mouse 216 and biofeedback headset 234 being operatively connected to the information handling system 200. For example, the mouse 216 and biofeedback headset controller 136 may be communicatively coupled to the information handling system 200 by a wire. These wires allow power and signals to be transceived between the biofeedback headset controller 136 and mouse 216 and the information handling system 200. The present specification further contemplates that this communicative coupling is wireless. In this embodiment, the physical distance between the mouse 216 and biofeedback headset 234 relative to the information handling system 200 may be increased thereby untethering the user physically from the information handling system 200. This may allow the user to move more freely than when the mouse 216 and biofeedback headset 234 are physically coupled to the processor of the information handling system 200 via a wired connection 250.

The game play the user engages in occurs as the processor of the information handling system 200 executes a gaming application. A gaming application may be any type of gaming application including, for example, first person shooter games, action games, adventure games, fighting games, puzzle games, role-playing games, simulation games, sports games, strategy games, racing games, and platform games, among others. It is appreciated that the type of game engaged in by the user may elicit certain stress levels and other physiological effects by the user. For example, the stress levels associated with a first-person shooter game may be vastly different than, for example, a puzzle game. The biofeedback headset 234 may be used to detect or determine when these gaming applications have elicited a physiological effect on the user and provide output to the user describing how to overcome any negative physiological effects. The biofeedback headset 234 may also be used in other environments such as with work applications, video conferencing applications, or other applications utilizing a headset in other embodiments.

In order to accomplish this, the biofeedback headset 234 includes a MOS gas sensor 242 in an embodiment. The MOS gas sensor 242 may be formed on a biofeedback headset printed circuit board (PCB) 238 and operatively coupled to a biofeedback headset controller 236 placed within the biofeedback headset 234. In an embodiment, the MOS gas sensor 242 is a gas sensor that includes a MEMS MOS gas sensor gas sensor to measure an amount of carbon dioxide ($CO_2$) at the mouthpiece. In an embodiment, the MOS gas sensor 242 may alternatively or additionally measure the $O_2$ composition of the air around the MOS gas sensor 242. During operation the MOS gas sensor 242 may be placed next to the user's mouth using, for example a mouthpiece. As the MOS gas sensor 242 is operating, the user may respirate causing the respirated air to be sensed the by MOS gas sensor 242. The MOS gas sensor 242 may measure the $CO_2$ and/or $O_2$ levels of the user's respirated breath and send those signals to the biofeedback headset controller 236.

This data may be presented to the processor 202 of the information handling system 200 via either the wired or wireless connection to the information handling system 200. The processor 202 may then execute a biofeedback headset machine learning system 246 and use the data received from the biofeedback headset controller 236 and MOS gas sensor 242, pressure sensor 244, or other data, as input to generate, when necessary, any warnings or indications to the user at the video/graphic display device 210 that respiration characteristics need to be changed. Other physiological effects on the user as the user may engage in game play at the information handling system 200 may be presented to the user based on the data retrieved from the MOS gas sensor 242. For example, detecting poor environmental air quality may be indicated to a user. Other physiological effects are contemplated by the present description. In an embodiment, the biofeedback headset machine learning system 246 may be used to also provide these different and additional warnings related to any changes that the user may have experienced based on the data provided by the biofeedback headset controller 236 and the sensors therein.

In an embodiment, the biofeedback headset 234 may include a pressure sensor 244. The pressure sensor 244 may be formed on the biofeedback headset printed circuit board (PCB) 238 and operatively coupled to a biofeedback headset controller 236 placed within the biofeedback headset 234. In an embodiment, the pressure sensor may include a micro-electromechanical systems (MEMS) capacitive pressure sensor. In an embodiment, the pressure sensor 244 may be placed within a mouthpiece in order to place the pressure sensor 244 at a location near the user's mouth. This will allow the pressure sensor 244 to detect a change in pressure above a base or threshold air pressure. In an embodiment, the base or threshold air pressure may be maintained through the use of a micro-fan fluidically coupled to the pressure sensor 244 in order to set a base air pressure at the pressure sensor 244. As the user breathes on the pressure sensor 244, the air pressure will change and this detected difference in air pressure may be sensed and provided to the biofeedback headset controller 236. The biofeedback headset controller 236 may pass the signals detected by the pressure sensor 244 to the processor 202 and biofeedback headset machine learning system 246 of the information handling system 200. Again, these signals may be used along with other data inputs as input to the biofeedback headset machine learning system 246 in order to provide the user with any type of biofeedback warnings or messages at the video/graphic display device 210.

In an embodiment, the biofeedback headset 234 may include a microphone 240. In an embodiment, the microphone 240 may be placed on a mouthpiece that is placed close to the user's mouth. In this embodiment, the microphone 240 is used to detect the user's voice and convert the audio into signals to be received at the biofeedback headset controller 236. Again, the biofeedback headset controller 236 may send the signals from the microphone 240 to the processor 202 of the information handling system 200. In an embodiment, the signals from the microphone 240 may be provided to the biofeedback headset machine learning system 246 as input.

In an embodiment, this input from the microphone 240 into the biofeedback headset machine learning system 246 may be related to the input from the pressure sensor 244. In this embodiment, the relation of the signals from the microphone 240 and the signals from the pressure sensor 244 may be used to determine a breathing rate of the user as the user engages with the gaming application. The breathing rate of the user may help indicate whether a message is to be presented to a user at the video/graphic display device 210 indicating that the user's breath rate is too slow or too fast. As the user engages with the game play, certain events experienced may cause the user to, for example, hold their breath or breath more repetitively. Each of these physiological changes in the user's breathing pattern may indicate that the user risks, for example, hypoxia or hyperventilation. As these conditions could lead to other, relatively more serious conditions such as anxiety, asthma, lung infections, or heart failure, the user may be provided with certain messages on the video/graphic display device 210 to pace their breathing. Additionally, a paced breathing state may increase the user's ability to accomplish goals during game play thereby increasing the ability of the user to be more effective. Because a more regulated breathing rate leads to better attentional and cognitive performances, the user is provided with the messages on the video/graphic display device 210 in order to increase their gaming abilities. Additionally, the messages presented to the user on the video/graphic display device 210 may relax the user and may more effectively engage the user in the game play while increasing the accessibility of any given user to increase their game play efficiency.

The gaming application inputs may be used as well as other I/O device responses may be measured and input into the biofeedback headset machine learning system 246 to determine physiological status of a user. Among one of these inputs may also include physical characteristics of the user. These physical characteristics may include a height, weight, age, and the like. As described herein, these characteristics of the user may also be used by the biofeedback headset machine learning system 246 to tailor any warning or status messages at the video/graphics display device 110.

As described herein, information handling system 200 may include a biofeedback headset machine learning system 246. The biofeedback headset machine learning system 246 may, in an embodiment, according to the present description, perform tasks related to providing, as output, data descriptive of when and which messages are presented to the user at the video/graphic display device 210. The biofeedback headset machine learning system 246 in an embodiment may, upon execution by the processor, determine such correlations between the data received from the MOS gas sensor 242, microphone 240, and pressure sensor 244, in an embodiment, based on any machine learning or neural network methodology known in the art or developed in the future. In a specific embodiment, the biofeedback headset machine learning system 246 may implement an unsupervised learning or supervised learning technique. For example, the biofeedback headset machine learning system 246 in an embodiment may model the relationships between the input data from the MOS gas sensor 242, microphone 240, and pressure sensor 244 and action during the game play within a gaming environment and result in physiological messages to the user at the video/graphic display device 210. The biofeedback headset machine learning system 246 may do this using, for example, a layered neural network topology. Such a neural network in an embodiment may include an input layer including a known, recorded set of data values from the MOS gas sensor 242, microphone 240, and pressure sensor 244 and an output layer including data descriptive of what and when physiological messages should be presented to a user. The biofeedback headset machine learning system 246 in an embodiment may propagate input through the layers of the neural network to project or predict what and when physiological messages should be presented to a user. Using a back-propagation method, the biofeedback headset machine learning system 246, in an embodiment, may then use the data from the MOS gas sensor 242, microphone 240, and pressure sensor 244 and game play characteristics to adjust weight matrices of the neural network describing the ways in which the data from the MOS gas sensor 242, microphone 240, and pressure sensor 244 are likely to affect what and when physiological messages should be presented to a user.

With the output layer, the information handling system 200 may provide what physiological messages should be presented to a user. The dataset related to the physiological messages that should be presented to the user may be used by the processor of the information handling system 200 executing a biofeedback headset machine learning system 246 to provide those messages commensurate with the game action during game play.

In an embodiment, the biofeedback headset machine learning system 246 may be initially trained by receiving, as training input, game play interaction of the user during the execution of the gaming application, intensity of the game play during the execution of the gaming application, a difficulty level during the execution of the gaming application, an opponent level difficulty during the execution of the gaming application, and teamwork level during the execution of the gaming application, the signals received from the MOS gas sensor 242, the signals received from the pressure sensor 244, and the signals received from the microphone 240, among other data related to the execution of the gaming application and use of the biofeedback headset 234 by the user. This input may be referred to herein as input data used to either train the biofeedback headset machine learning system 246 or provide input in real-time in order to receive as output indications of a physiological state of a user implementing the biofeedback headset 234.

In an embodiment, the biofeedback headset machine learning system 246 may be code instructions and may operate with the main memory 204, the processor 202, the video/graphic display device 210, the keyboard 214, and the network interface device 220 via bus 208, and several forms of communication may be used, including ACPI, SMBus, a 24 MHZ BFSK-coded transmission channel, or shared memory. Driver software, firmware, controllers, and the like may communicate with applications on the information handling system 200. During this process and after the biofeedback headset machine learning system 246 has been trained (which may occur remotely), the processor 202 may receive the output from a trained inference model of the biofeedback headset machine learning system 246 that defines the indications of a physiological state of a user implementing the biofeedback headset 234. Upon receipt of this dataset, the processor 202 may cause these indications to be presented to the user at the video/graphic display device 210.

By way of example, the output from the biofeedback headset machine learning system 246 may indicate that the user is breathing to heavily which may result in both adverse health effects as well as poor gaming performance. As a result, the processor 202 may provide a message to appear on the video/graphic display device 210 indicating to the user that the breath rate is too frequent and that the user should slow the rate of breathing. In order for the biofeedback headset machine learning system 246 to provide such indication, the breath rate data from the microphone 240 and pressure sensor 244 as well as the air composition data from the MOS gas sensor 242 may be used as input into the biofeedback headset machine learning system 246 and, based on other factors such as the game play the user is engaged in, may provide an appropriate indicator to the user. This indicator, in an embodiment, may include a message flashed across the screen. In an embodiment, the indicator may be an icon placed within a system tray or other notification area usually placed along a lower edge of the viewable surface of the video/graphic display device 210. In an embodiment, the indicator may be an audio indicator presented to the user via one or more speakers within the biofeedback headset 234. The present specification contemplates that any or all of these examples may be used to indicate a specific biofeedback message to the user during game play. In this manner, a user may be presented with appropriate biofeedback that increases the user's attentional and cognitive performance when the user is engaged in game play. This may allow the user to enjoy the game play as well as allow the user to engage with the game play for a longer duration of time due to the reduced mental and bodily stress exerted on the user.

Figure 3:
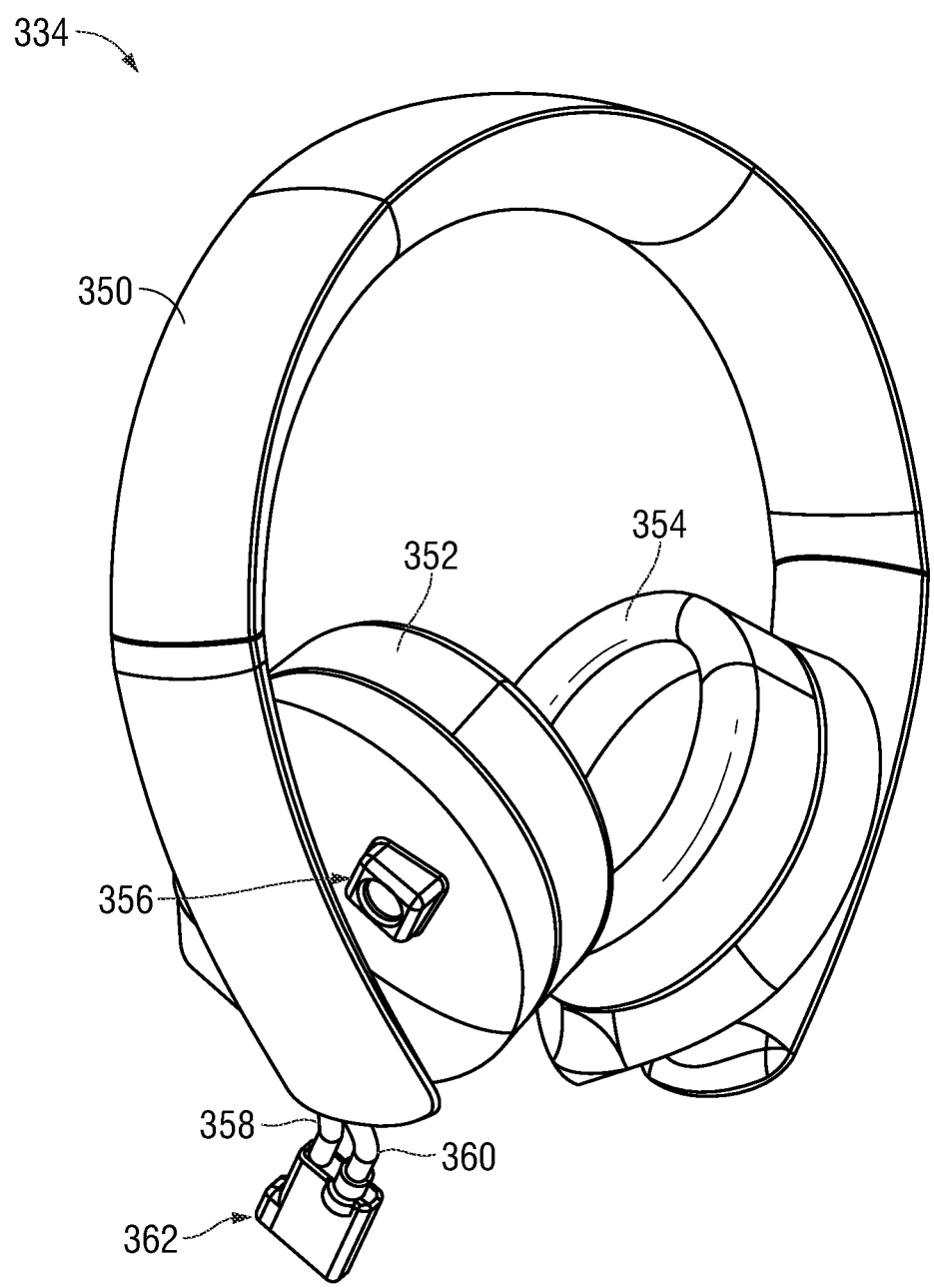
FIG. 3 is a rear, perspective graphical diagram view of a biofeedback headset according to an embodiment of the present disclosure.
Figure 4:
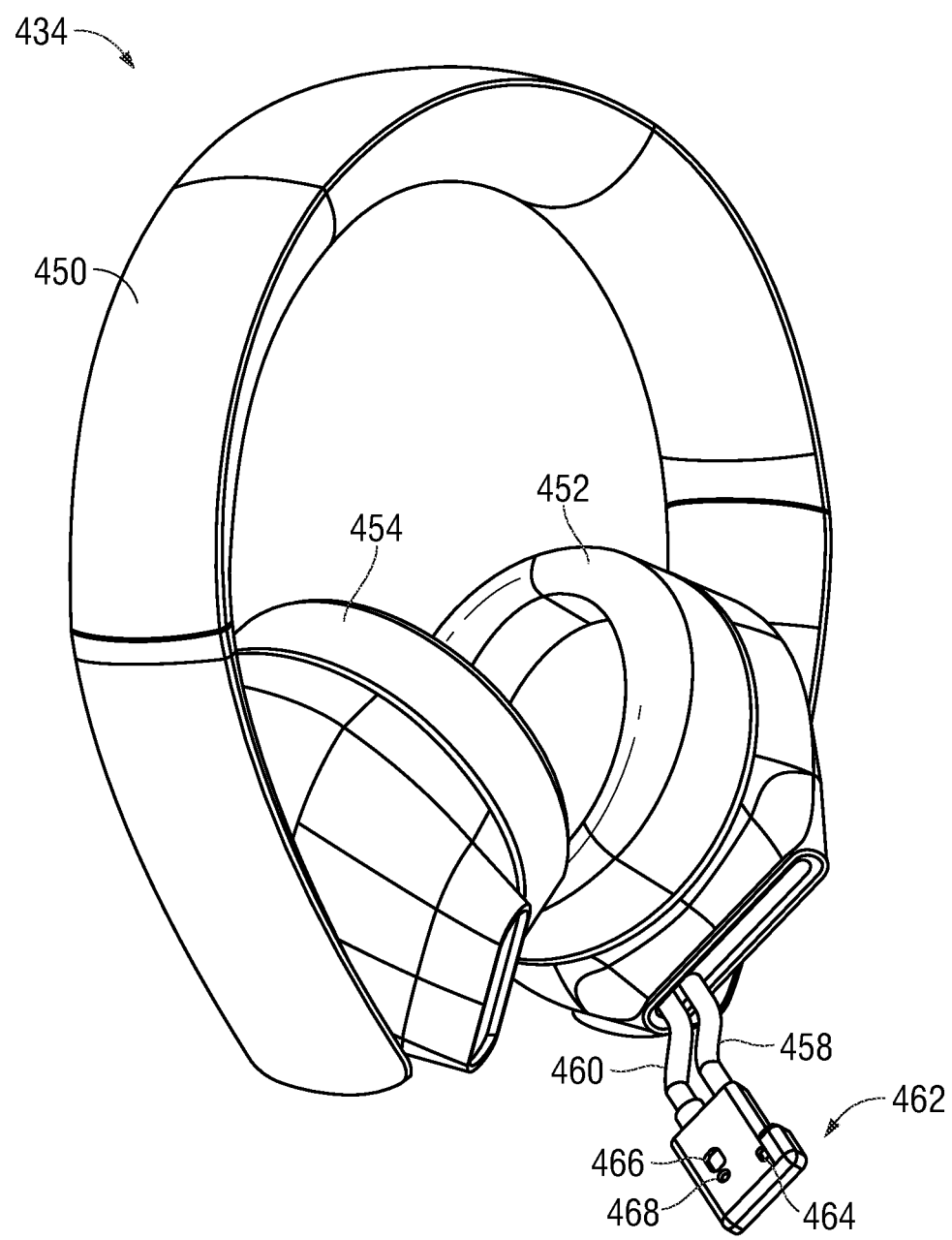
FIG. 4 is a front, perspective graphical diagram of the biofeedback headset according to an embodiment of the present disclosure.

FIG. 3 is a rear, perspective graphical diagram view of a biofeedback headset 334 according to an embodiment of the present disclosure. FIG. 4 is a front, perspective graphical diagram of the biofeedback headset 434 according to an embodiment of the present disclosure. The biofeedback headset 334, 434 shown in FIGS. 3 and 4 are shown to be formed into one of either a circumaural (aka: "over-the-ear") headphone or supra-aural (aka: "on-the-ear") headphone. In an embodiment, the biofeedback headset 334, 434 may include a pair of speakers in the form of these type of earphones 352, 354, 452, 454 arranged on the biofeedback headset 334, 434, or the audio output from the information handling system may be provided by, for example, a speaker system at the information handling system in some embodiments. For the purpose of convenience in explanation herein, the biofeedback headset 334, 434 is described as an over-the-ear-type biofeedback headset 334, 434 where audio is provided to a user's ears via a speaker placed within each of a left earphone 352, 452 and right earphone 354, 454. In an embodiment, the left earphone 352, 452 and right earphone 354, 454 may be operatively coupled together via a headband 350, 450. The position of the left earphone 352, 452 and right earphone 354, 454 relative to the headband 350, 450 may be adjustable to fit any given user's head shape for optimal comfort.

The biofeedback headset 334, 434 may include a mouthpiece 362, 462. The mouthpiece 362, 462 may be a portion of the biofeedback headset 334, 434 that extends out from one of the left earphone 352, 452 or right earphone 354, 454 such that the mouthpiece 362, 462 is placed at or operatively near a user's mouth. Whether the mouthpiece 362, 462 is operatively near the user's mouth may depend on whether a MOS gas sensor, microphone, and pressure sensor formed within the biofeedback headset 334, 434 can detect the composition of air expelled from the user's mouth, the sounds from the user's mouth, and the pressure of a user's breath against the mouthpiece 362, 462, respectively. In an embodiment, the mouthpiece 362, 462 may be made to be adjustable such that the MOS gas sensor, microphone, and pressure sensor within the mouthpiece 362, 462 are placed directly in front of the user's mouth.

The mouthpiece 362, 462 may include a housing (not shown) that houses, among other elements, a microphone signal tube 358, 458 and a MEMS air tube 360, 460. The microphone signal tube 358, 458 may house a wire that leads from a microphone housed in the mouthpiece 362, 462 to a biofeedback headset controller housed within the biofeedback headset 334, 434 or conduct soundwave from the tube 358, 458 to a microphone element. The microphone is placed within the mouthpiece 362, 462 in order to detect sounds from the user's mouth and provide signals to the biofeedback headset controller representative of a pitch, frequency, and magnitude, of those sounds. In an embodiment, the microphone may detect the sound of a user's breath rate and the signals received by the biofeedback headset controller may discern a breath rate that may be used as input to the biofeedback headset machine learning system as described herein. In order for the sounds from the user's mouth to reach the microphone, the mouthpiece 362, 462 may include a sound access port 464. The sound access port 464 may be a hole formed within the mouthpiece 362, 462 so that sounds may reach the microphone or air tube 358, 458 placed directly under the sound access port 464.

The biofeedback headset 334, 434 may include a gas sensor as described. The gas sensor may be, in an embodiment, a MEMS MOS gas sensor that detect a composition of air the user respirates such as an amount of $CO_2$ and/or $O_2$ respirated by the user. In order to provide an accurate reading of the composition of air at the MEMS MOS gas sensor, the MEMS air tube 360, 460 may operatively couple the MEMS MOS gas sensor to a micro-fan. In an embodiment, the micro-fan formed into the right earphone 354, 454 or left earphone 352, 452 may be fluidically coupled to the MEMS MOS gas sensor so that the micro-fan can draw air across the MEMS MOS gas sensor, through the MEMS air tube 360, 460 and out a vent 356 formed into the right earphone 354, 454 or left earphone 352, 452. The amount of air pulled across the MEMS MOS gas sensor by the micro-fan may be made to remain stable such that a representative composition of air at the MEMS MOS gas sensor may be detected. In an embodiment, the air composition may have various levels of carbon-dioxide ($CO_2$) and oxygen ($O_2$) that indicates a state of the respiration functions of the user. For example, where the user is breathing heavily, the amount of either $CO_2$ or $O_2$ may increase or decrease. With data from the microphone, the data received from the MEMS MOS gas sensor may be used to provide messages to the user to, for example, describe how to increase or decrease the user's rate of breath. Other messages may be presented based on the data received at the biofeedback headset machine learning system as input as described herein. In order to detect the air composition at the MEMS MOS gas sensor, the mouthpiece 362, 462 may include a MEMS MOS gas sensor access port 466 formed in the mouthpiece 362, 462. The MEMS MOS gas sensor access port 466 may allow air from the user's mouth to reach the MEMS MOS gas sensor placed within the MEMS MOS gas sensor access port 466.

The biofeedback headset 334, 434 may further include a pressure sensor. In an embodiment, the pressure sensor may include a microelectromechanical systems (MEMS) capacitive pressure sensor that detects a change in pressure above a base or threshold air pressure. In order to provide an accurate reading of the air pressure at the pressure sensor, the MEMS air tube 360, 460 may operatively couple the pressure sensor to a micro-fan. In an embodiment, the micro-fan formed into the right earphone 354, 454 or left earphone 352, 452 may be fluidically coupled to the pressure sensor so that the micro-fan can draw air across the pressure sensor, through the MEMS air tube 360, 460 and out a vent 356 formed into the right earphone 354, 454 or left earphone 352, 452. The amount of air pulled across the pressure sensor by the micro-fan may be made to remain stable such that a representative air pressure at the pressure sensor may be maintained in situations where the use is not breathing on the pressure sensor. When the user is not breathing on the pressure sensor, the air pressure detected at the pressure sensor may be determined to be a baseline air pressure. As the user begins and continues to breath onto the pressure sensor the air pressure detected changes beyond a threshold amount. As the threshold amount of change in air pressure is met, the pressure sensor may send this air pressure data to the biofeedback headset controller formed within the biofeedback headset 334, 434. In an embodiment, with data from the microphone and/or MEMS MOS gas sensor, the data received from the pressure sensor may be used to provide messages to the user to, for example, describe how to increase or decrease the user's rate of breath. Other messages may be presented based on the data received at the biofeedback headset machine learning system as input as described herein. In order to detect the air pressure at the pressure sensor, the mouthpiece 362, 462 may include a pressure sensor access port 468 formed in the mouthpiece 362, 462. The pressure sensor access port 468 may allow air from the user's mouth to reach the pressure sensor placed within the pressure sensor access port 468.

Figure 5:
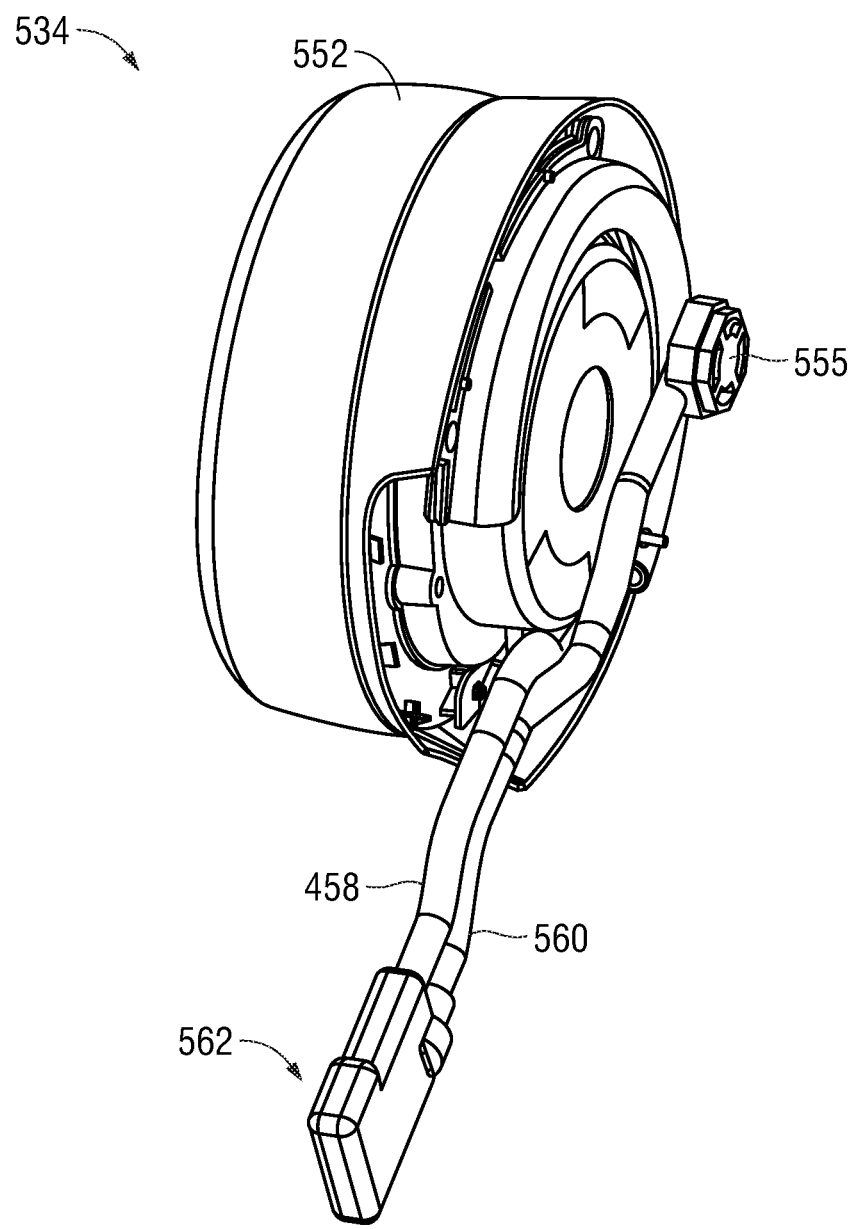
FIG. 5 is a perspective, cut-away graphical diagram of an earpiece of a biofeedback headset according to an embodiment of the present disclosure.
Figure 6:
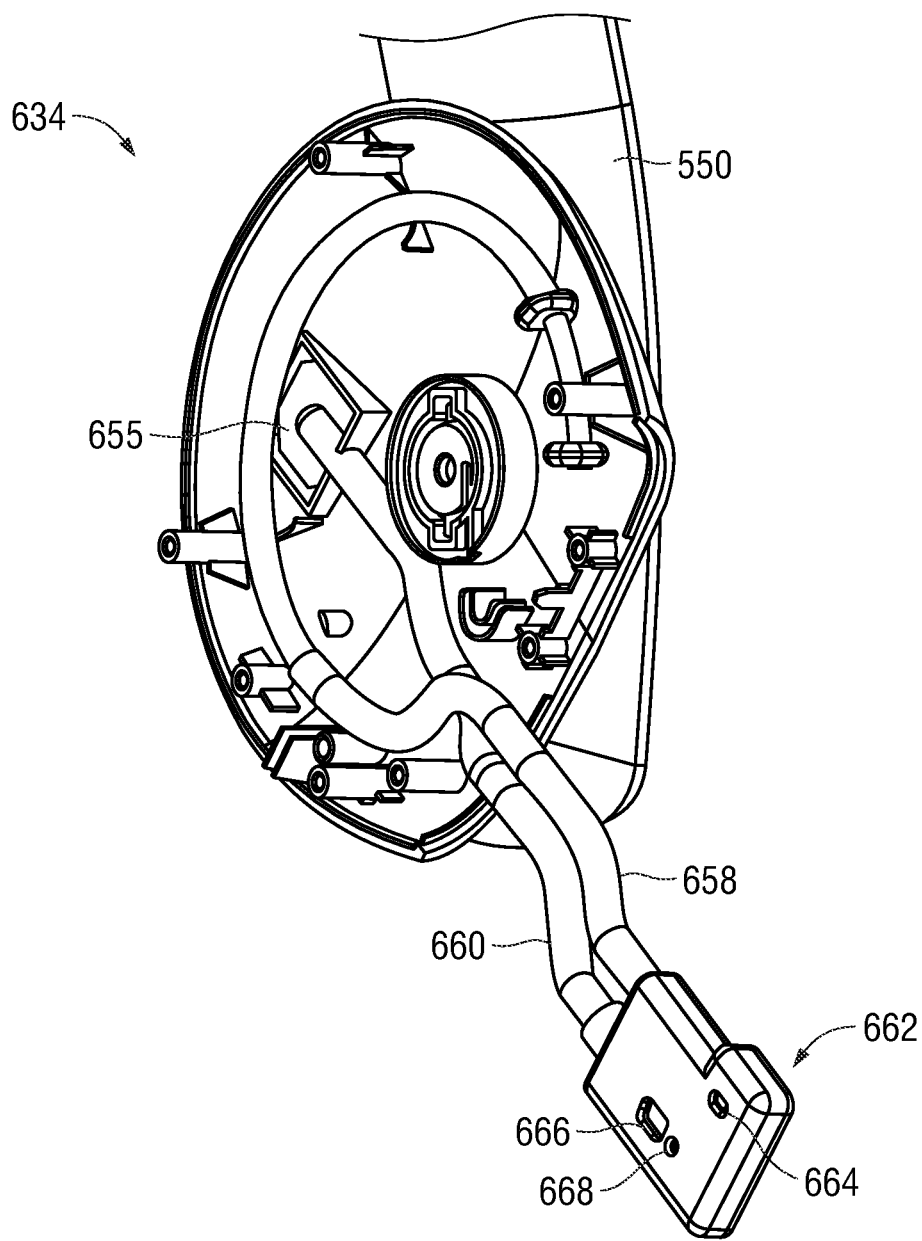
FIG. 6 is a perspective, cut-away graphical diagram of an earpiece of a biofeedback headset according to another embodiment of the present disclosure.

FIG. 5 is a perspective, cut-away graphical diagram of an earpiece 552 of the biofeedback headset 534, 634 according to an embodiment of the present disclosure. FIG. 6 is a perspective, cut-away graphical diagram of an earpiece of a biofeedback headset 534, 634 according to another embodiment of the present disclosure. In FIGS. 5 and 6, the earpiece 552 shown is a left earphone (e.g., 352, 452) shown in FIGS. 3 and 4. However, the earpiece 552 may alternatively be a right earphone (e.g., 354, 454) as shown in FIGS. 3 and 4 without going beyond the principals described herein. Additionally, FIG. 5 shows the earpiece 552 with a mouthpiece 562, MEMS air tube 560, microphone signal tube 558, and micro-fan 555, 655 coupled thereto while FIG. 6 shows the mouthpiece 562, MEMS air tube 560, microphone signal tube 558, and micro-fan 555, 655 coupled to an exterior housing of the earpiece 552 that is further coupled to the headband 550 of the biofeedback headset 534, 634.

FIGS. 5 and 6 show an interface between the MEMS air tube 560, 660 and microphone signal tube 558, 658 and the housing of the earpiece 552. As described herein, the MEMS air tube 560, 660 is fluidically couples the MOS gas sensor and pressure sensor to a micro-fan 555, 655. The MEMS air tube 560, 660 may be hollow throughout so that an amount of air may be drawn from the MEMS MOS gas sensor access port 666 and pressure sensor access port 668 by the micro-fan 555, 655. Additionally, any signal wiring or cabling operatively coupling the MOS gas sensor and pressure sensor to a biofeedback headset controller may be passed, coaxially, through this MEMS air tube 560, 660 in an embodiment. The wiring from the MOS gas sensor and pressure sensor may exit the MEMS air tube 560, 660 at any point in order to be operatively coupled to the biofeedback headset controller. Where the wiring exits the MEMS air tube 560, 660, a fluidic seal may be provided so that any amount of air drawn through the MEMS air tube 560, 660 does not leak out from the MEMS air tube 560, 660. In a specific embodiment, the wiring from the MOS gas sensor and pressure sensor may exit the MEMS air tube 560, 660 at the back of the micro-fan 555, 655. In other embodiments, the wiring may be placed external to the MEMS air tube 560, 660 to operatively connect the MOS gas sensor and pressure sensor to the biofeedback headset controller.

As described herein, the micro-fan 555, 655 provides a constant flow of air over the MOS gas sensor and pressure sensor. In order to do this the mouthpiece 562, 662 includes a MEMS MOS gas sensor access port 666 and a pressure sensor access port 668 so that air (e.g., respirated air from the user and surrounding air at the mouthpiece 562, 662) may be drawn into the mouthpiece 562, 662, across the MOS gas sensor and pressure sensor, through the MEMS air tube 560, 660, and to the micro-fan 555, 655 to be vented out of the earpiece 552 at a vent such as vent 356 shown in FIG. 3. The amount of air drawn by the micro-fan 555, 655 may be constant in some embodiments so that changes in pressure and detected air composition as the pressure sensor and MOS gas sensor, respectively, is properly detected as described herein.

The biofeedback headset 534, 634 in another embodiment also includes a microphone signal tube 558, 658 that houses, coaxially, any wiring that operatively couples the microphone in the mouthpiece 562, 662 to the biofeedback headset controller. This microphone signal tube 558, 658 may provide support to this wiring so that loose wires are not exposed to any manipulation by the user during operation of the biofeedback headset 534, 634. In one embodiment, the microphone signal tube 558, 658 can also be an air tube to a microphone membrane element in the earpiece. In this embodiment, sound from the user may pass down the length of the microphone signal tube 558, 658 and reach the microphone membrane element to convert that sound to audio signals. In an embodiment, a sound access port 664 may be formed in the mouthpiece 562, 662 so that sounds from the user's mouth may reach the microphone placed behind and within the sound access port 664 or at the end of the air tube leading to the microphone as described.

As described herein, the earpiece 552 may include any additional devices used to provide, in an embodiment, the user with audio output from the information handling system. The biofeedback headset 534, 634 may, therefore, include small loudspeaker drivers, electroacoustic transducers and other types of devices the provide this audio output to the user. In an embodiment, the loudspeaker drivers may relay audio output to the user representative of sounds produced during game play by a gaming application. In an embodiment, these sounds may include audio warnings or messages descriptive of any physiological effects the user is experiencing during the game play. Thus, along with any visual warnings or messages presented to the user at, for example, a video/graphic display device (e.g., 110 in FIG. 1), the user may be presented with similar warnings and messages in an auditory form at the small loudspeaker drivers formed in the biofeedback headset 534, 634.

In an embodiment, the mouthpiece 562, 662, MEMS air tube 560, 660, and microphone signal tube 558, 658 may be adjustable by the user. This may be done, for example, with the use of any hinging or rotation devices that allow the user to move these components such that the mouthpiece 562, 662 is placed at the user's mouth during use of the biofeedback headset 534, 634.

Figure 7:
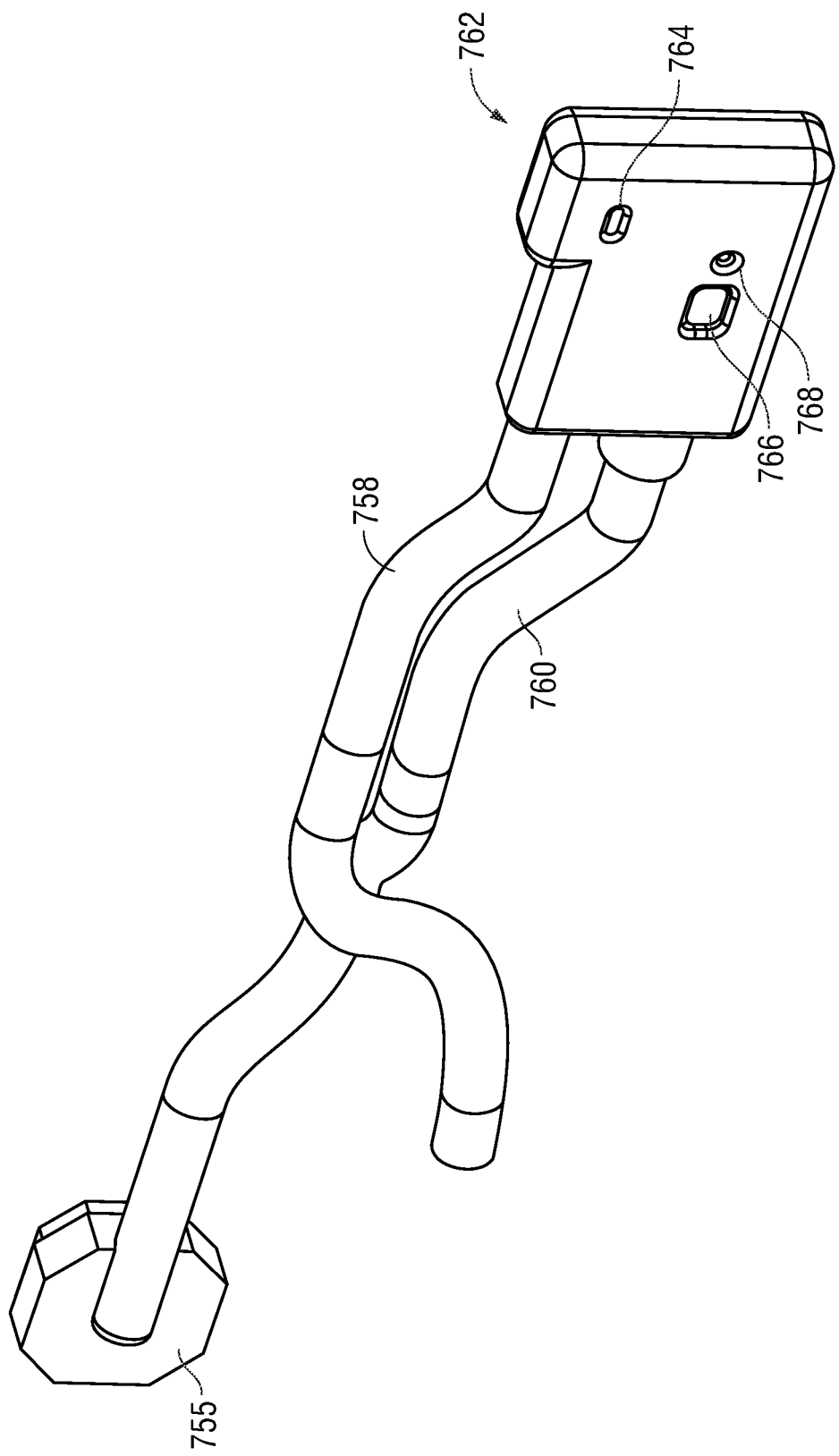
FIG. 7 is a perspective, cut-away graphical diagram of a mouthpiece of a biofeedback headset according to an embodiment of the present disclosure.

FIG. 7 is a perspective, cut-away graphical diagram of a mouthpiece 762 of a biofeedback headset according to an embodiment of the present disclosure. FIG. 7 shows a more detailed view of the interface between the mouthpiece 762 and the MEMS air tube 760 and microphone signal tube 758 in an embodiment. Still further, FIG. 7 shows a more detailed view of the interface between the MEMS air tube 760 and the micro-fan 755. The microphone signal tube 758 in FIG. 7 is shown in a truncated form, but the present application contemplates that the microphone signal tube 758 may extend further so that the air tube or wiring for the microphone and biofeedback headset controller can be contained therein. Again, the microphone signal tube 758 can be an air tube or a tube to contain wires for the microphone. In these embodiments, the microphone membrane used to interact with the sounds from the user may be located in the mouthpiece or the ear piece.

In order to prevent air from leaking from the MEMS air tube 760, the mouthpiece 762 may include any jacketing or air seal between the MEMS air tube 760 and the housing of the mouthpiece 762. In these examples, the passage of air from the mouthpiece 762 to the micro-fan 755 may be limited to the amount of air that passes through the pressure sensor access port 768 and the MEMS MOS gas sensor access port 766. In a specific embodiment, the MOS gas sensor and pressure sensor are hermetically sealed within the mouthpiece 762 from the microphone and its sound access port 764 so that air is not taken into the mouthpiece 762 via the sound access port 764.

Figure 8:
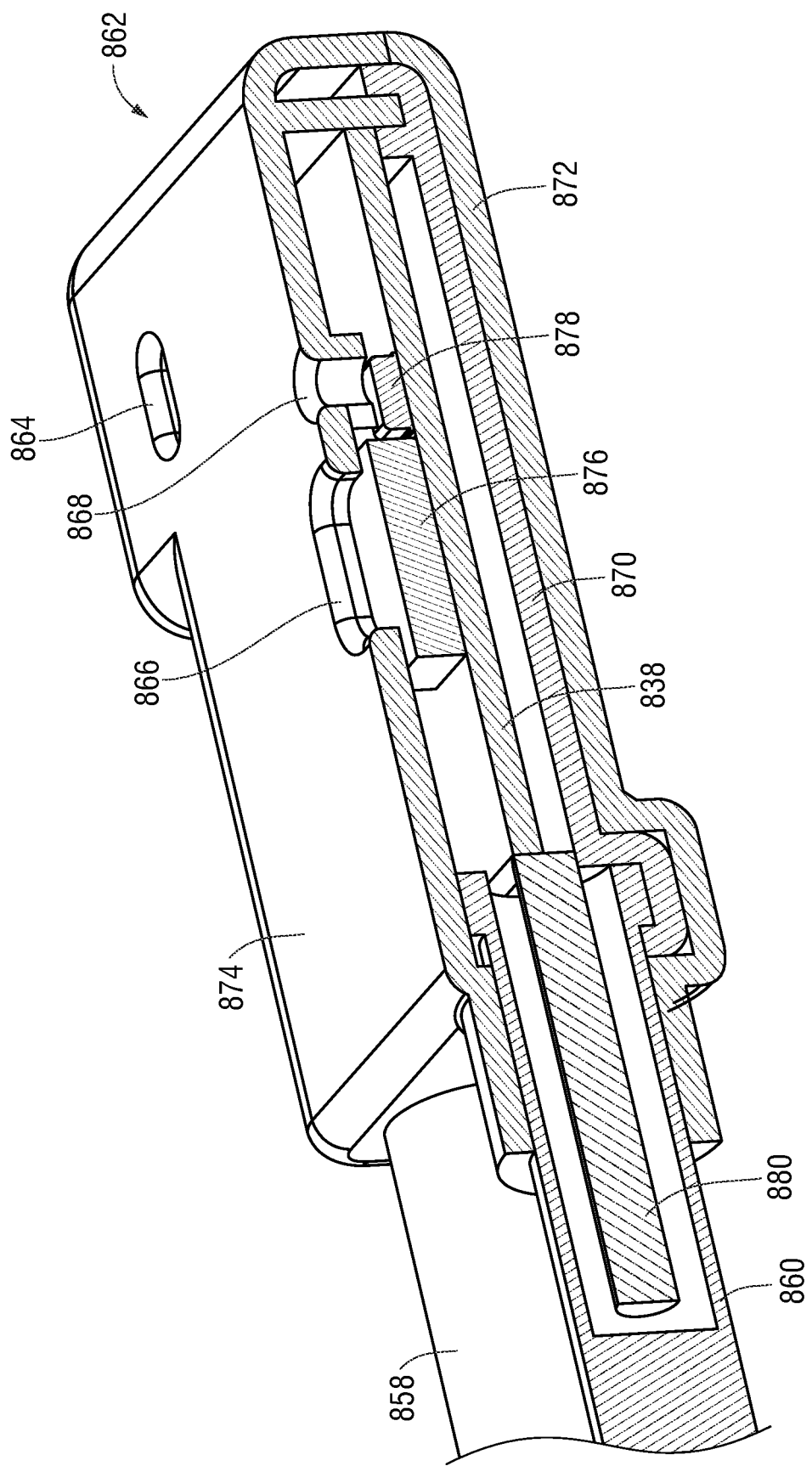
FIG. 8 is a perspective, cut-away graphical diagram of a mouthpiece of a biofeedback headset according to another embodiment of the present disclosure.
Figure 9:
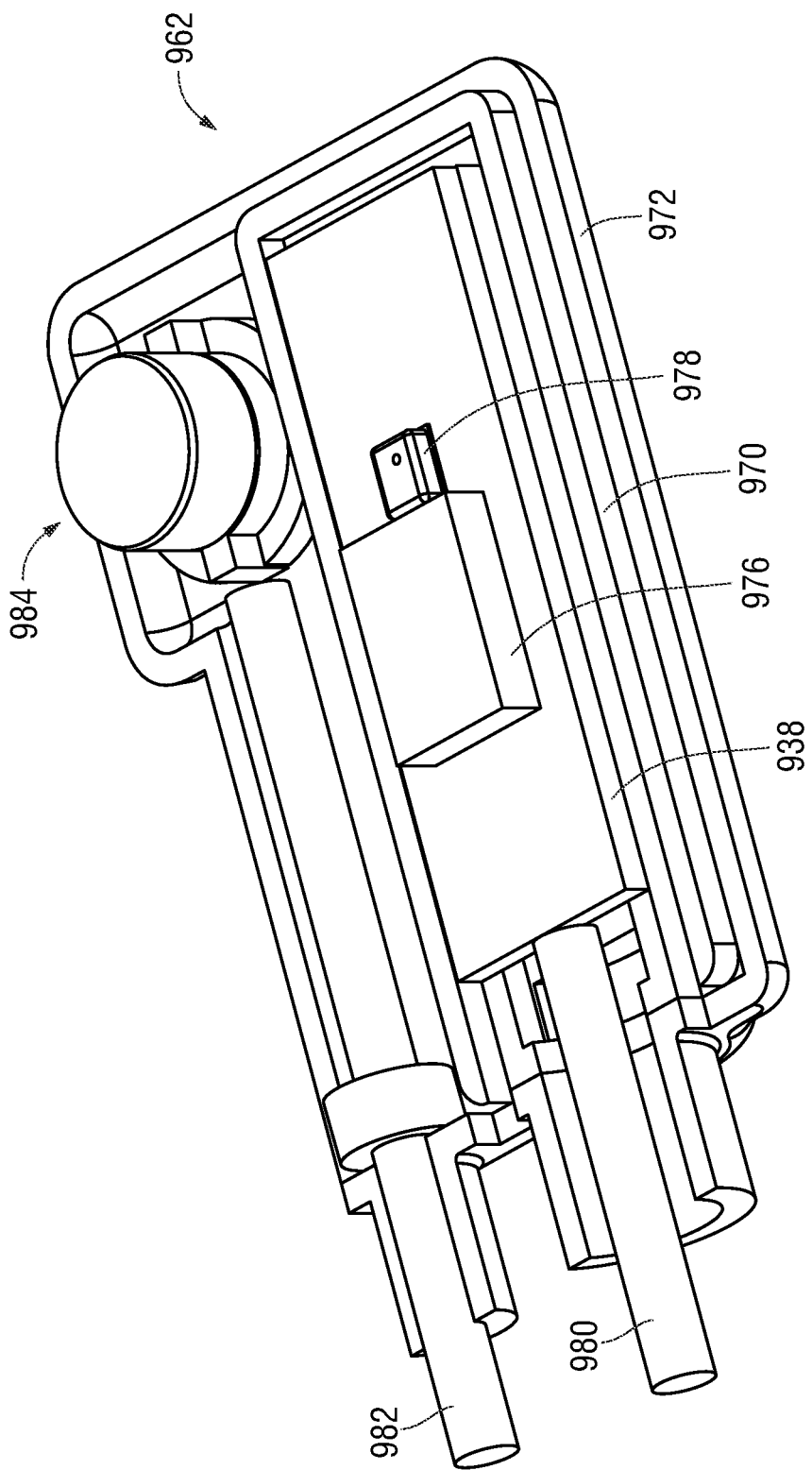
FIG. 9 is a perspective, cut-away graphical diagram of a mouthpiece of a biofeedback headset according to another embodiment of the present disclosure.
Figure 10:
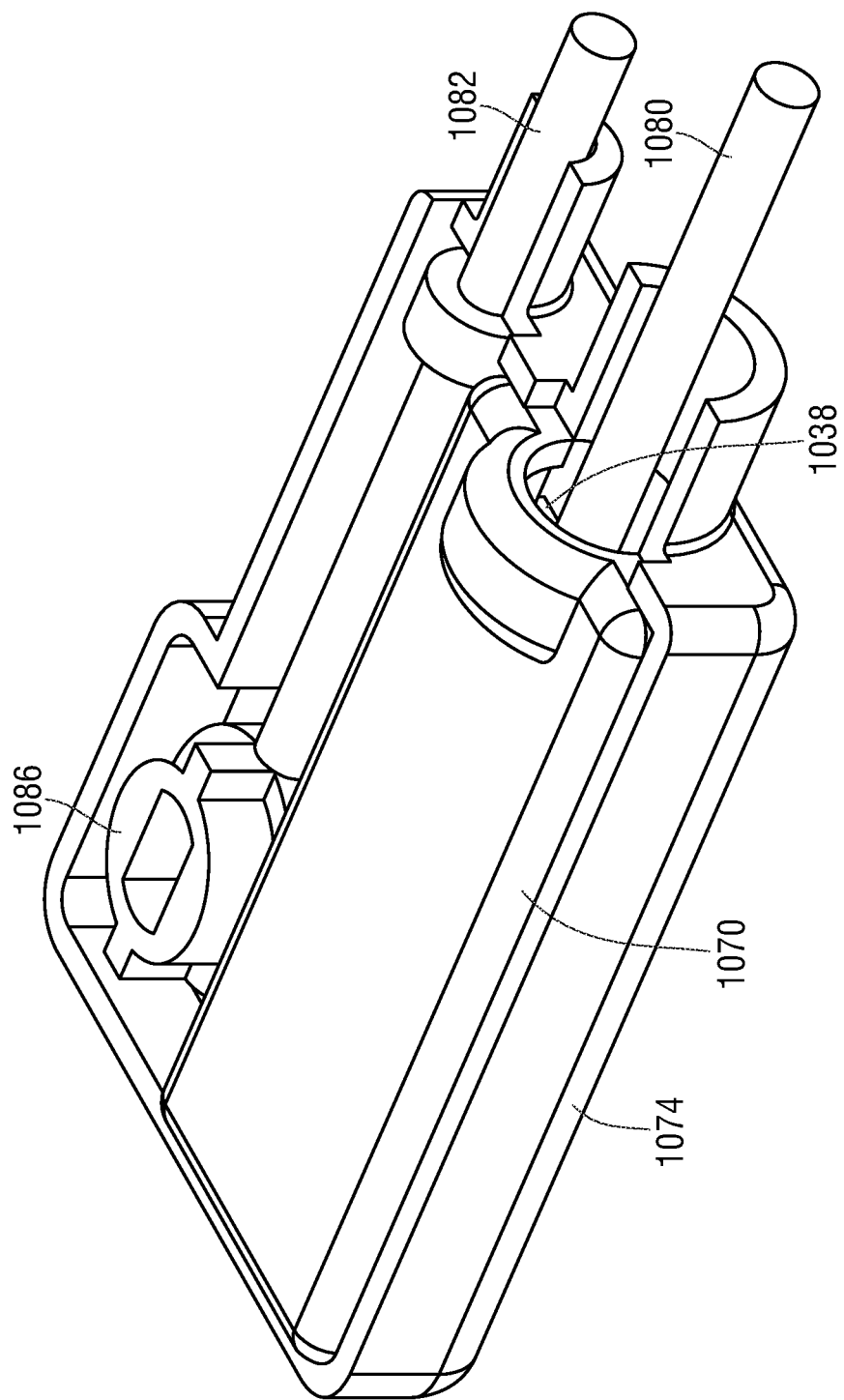
FIG. 10 is a perspective, cut-away graphical diagram of a mouthpiece of a biofeedback headset according to another embodiment of the present disclosure.

FIG. 8 is a perspective, cut-away graphical diagram of a mouthpiece 862 of a biofeedback headset according to another embodiment of the present disclosure. FIG. 9 is a perspective, cut-away graphical diagram of a mouthpiece 962 of a biofeedback headset according to another embodiment of the present disclosure. FIG. 10 is a perspective, cut-away graphical diagram of a mouthpiece 1062 of a biofeedback headset according to another embodiment of the present disclosure.

FIGS. 8, 9, and 10 show a housing used to secure the MOS gas sensor 876, 976, 1076 and pressure sensor 878, 978, 1078 formed on a biofeedback headset PCB 838, 938, 1038. This housing may include a top housing 874, 1074 that is made to mate with a bottom housing 872, 972 to house the pressure sensor 878, 978, 1078, MOS gas sensor 876, 976, 1076, and a microphone 984 therein. The top housing 874, 1074 and bottom housing 872, 972 may further house a rubber-sealed chamber sealing the pressure sensor 878, 978, 1078 and MOS gas sensor 876, 976, 1076 from the microphone 984 using a rubber gasket 870, 970, 1070, for example. As described herein, this rubber-sealed chamber may prevent air passing into the pressure sensor access port 868 and MEMS MOS gas sensor access port 866 from exiting this rubber-sealed chamber. The rubber gasket 870, 970, 1070 may also prevent air being drawn in from the sound access port 864 during activation of the micro-fan fluidically coupled to the MOS gas sensor 876, 976, 1076 and pressure sensor 878, 978, 1078 via the MEMS air tube 860. This hermetically seals the airflow across or over the pressure sensor 878, 978, 1078 and MOS gas sensor 876, 976, 1076 from the microphone 984 as described herein. In an embodiment, the rubber gasket 870, 970, 1070, top housing 874, 1074, and bottom housing 872, 972 may prevent certain amounts of water or other contaminants from entering the mouthpiece 862, 962, 1062 and damaging the microphone 984, MOS gas sensor 876, 976, 1076, or pressure sensor 878, 978, 1078.

As described herein, the MEMS air tube 860 may have a MOS gas sensor and pressure sensor signal wire 880 formed coaxially therethrough. The MOS gas sensor and pressure sensor signal wire 880 may be operatively coupled to the MOS gas sensor 876, 976, 1076 and pressure sensor 878, 978, 1078 via any circuitry formed onto the biofeedback headset PCB 838, 938, 1038. Similarly, the microphone signal tube 858 may house, coaxially, a microphone signal wire 982, 1082 that operatively couples the microphone 984 to a biofeedback headset controller in the biofeedback headset or may be an air tube to a microphone membrane element in the ear piece.

The mouthpiece 862, 962, 1062 may further include a microphone damper 1086. The microphone damper 1086 may be placed around the microphone 984 in order to dampen any external noises that may affect the quality of the audio picked up by the microphone 984. Where the microphone damper 1086 is not present, the sounds picked up by the microphone 984 may have a hollow or echo sound associated with them due to the sounds being allowed to reverberate with the housing of the mouthpiece 862, 962, 1062.

Figure 11:
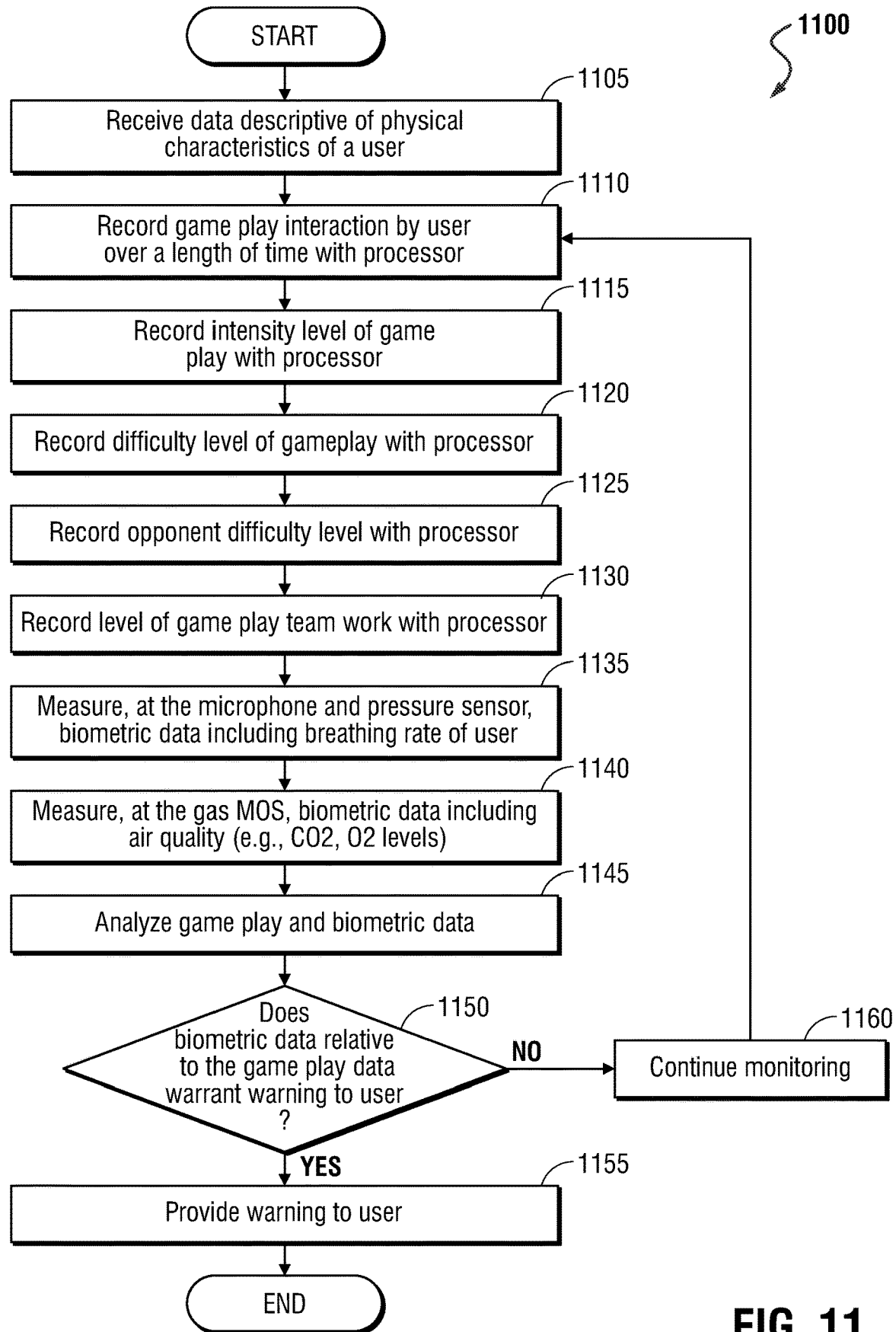
FIG. 11 is a flow diagram illustrating a method of providing physiological messages to a user based on data received from a biofeedback headset and gaming application according to an embodiment of the present disclosure.

FIG. 11 is a flow diagram illustrating a method 1100 of providing physiological messages to a user based on data received from a biofeedback headset and gaming application according to an embodiment of the present disclosure. The method 1100 may include, at block 1105, receiving data descriptive of any physical characteristics of a user engaged in the game play of the gaming application. These physical characteristics may include a height, weight, and age of the user, among other characteristics. As described herein, these characteristics of the user may also be used by the biofeedback headset machine learning system to tailor any warning or status messages at the video/graphics display device.

The method 1100 may also include, at block 1110, recording game play interaction by a user over a length of time with a processor of the information handling system. This recorded game play and define certain actions conducted by the user to interact with certain in-game objects and environments. By way of example, the gaming application being executed by the processor of the information handling system may be a first-person shooter gaming application. In this example, the first-person shooter gaming application may involve gun and other weapon-based combat scenarios in a first-person perspective such that the player experiences the action through the eyes of the avatar used by the player to advance through the gaming environment. Here the method 1100 may record which weapons the avatar interacts with, what environments the avatar is present in, which events occur within the gaming environment, among other attributes of the game play.

The method 1100 may include recording an intensity level of game play with the processor of the information handling system at block 1115. The intensity of the game play may vary from one gaming application to another and even during the execution of a single gaming application. The varying intensity experienced by the user during game play may affect the user's ability to be as effective at winning or otherwise achieving certain goals set out in the game play. Following with the example of the first-person gaming application, the method 1100 at block 1115 may record those scenarios where, for example, the avatar confronts an obstacle to overcome such as a shootout or other intense scene where action is occurring relatively quickly and action is needed to survive. Additionally, the processor of the information handling system may record those scenarios within the game play that are otherwise mundane or include respites where the user may regroup and prepare for future encounters.

The method 1100 may also include, at block 1120, recording a difficulty level of the game play using the processor of the information handling system. This difficulty level may be based on the progress made by the user throughout the gaming scenarios or may be selected as a universal gaming setting such as low difficulty, medium difficulty, extreme difficulty, master mode, or other types of game play difficulty levels. In the case of the example first-person shooting gaming application, this difficulty level may be set by the user prior to initiating game play or may be increased as a result of the user's progression through a number of boards or levels presented to the user in the course of the game play.

The method 1100 may further include recording any opponent difficulty level using the processor of the information handling system at block 1125. In the example of the first-person shooter gaming application this variable may also be based on the difficulty level selected by the user prior to initiating game play as well as the progression through the gaming environment. For example, the difficulty level of any given opponent may vary depending on whether the opponent is a "bot" or other computer-generated opponent, what level that bot is encountered within the game play, and whether the opponent is an avatar operated by a live human being during, for example, an online interaction.

The method 1100 may further include, at block 1130, recording the level of game play team work with the processor of the information handling system. In some embodiment gaming applications, a team may be formed, usually via an online gaming application, in order to accomplish goals within the gaming application together. In the context of the first-person shooter gaming application, the user may elicit help from certain real-life or internet-acquainted friends to achieve these goals. This may, in some embodiments, increase the level of stress or decrease the level of stress based on how well the user interacts with others. Accordingly, such a scenario may affect the game play of the user for good or bad.

The method 1100 may further include measuring, at the microphone and pressure sensor formed in a mouthpiece of the biofeedback headset, biometric data including a breathing rate of the user at block 1135. The breathing rate of the user may vary from time to time based on physical exertion or, in the case of game play, excitement or stress encountered during the game play. Often a user may fidget or otherwise engage in repetitive physical movements during stressful situations experienced during game play. This too may add to an increased breath rate of the user. In the context of the first-person shooter gaming application, the user may experience those higher breathing rates when the intensity level of the game play is increased or the difficulty level has been increased. Additionally, a user's breath rate may decrease when the intensity level is decreased and when the difficulty level of the game play is also decreased.

The method 1100 may continue at block 1140 with measuring, at the gas MOS gas sensor, biometric data that includes a measurement of the air quality of the breath respirated by the user. In some embodiments, the ambient air quality is also measured along with the respirated breath from the user. For example, levels of ambient $O_2/CO_2$ may be detected within an amount of air drawn in before or after a breath from the user. Inhaled air may be detected for levels of ambient gases to assess ambient air quality in an example embodiment. In another example embodiment, the gas MOS gas sensor may detect an amount of $CO_2$ and/or $O_2$ respirated by the user during any scenario experienced during game play. Again, in the context of a first-person shooter gaming application, the air quality or composition of air detected at the gas MOS gas sensor may show that during intense scenarios of the game play, the amount of $CO_2$ and/or $O_2$ respirated by the user may go up or down based on the amount of air respirated as well as the frequency of respiration. In other embodiments, the user may be notified of poor room air quality requiring better ventilation.

The method 1100 may further include, at block 1145, analyzing the game play and biometric data at the processor in order to determine which, if any, physiological message or warning to present to the user based on that data. The analysis may be completed using the biofeedback headset machine learning system described herein. The biofeedback headset machine learning system may be implemented to monitor for potential health issues associated with the user engaged in game play and provide health messages to a user during this game play. In the context of the present embodiment, the biofeedback headset machine learning system uses, as input, the biofeedback signals from the pressure sensor and MOS gas sensor as well as the recorded data described at blocks 1110-1130 and user physical characteristics at block 1105 in order to provide, as output, health messages to the user. The biofeedback headset machine learning system, in an embodiment may, upon execution by the processor, determine such correlations between the data received from the MOS gas sensor, microphone, and pressure sensor based on any trained machine learning or neural network methodology known in the art or developed in the future. In a specific embodiment, the biofeedback headset machine learning system may implement an unsupervised learning or supervised learning technique to establish a correlation between game play conditions and biofeedback signals and user data as in steps 1105-1140 with possible biometric feedback warnings or status updates. The biofeedback headset machine learning system may provide this output, for example, using a layered neural network topology trains as a multilevel classifier. Such a neural network in an embodiment may include an input layer including a known, recorded set of data values from the MOS gas sensor, microphone, and pressure sensor along with the recorded gaming data and an output layer including data descriptive of what and when physiological messages should be presented to a user. The biofeedback headset machine learning system in an embodiment may propagate input through the layers of the neural network to project or predict what and when physiological messages should be presented to a user. Using a back-propagation method, the biofeedback headset machine learning system, in an embodiment, may then use the data from the MOS gas sensor, microphone, and pressure sensor and game play characteristics to adjust weight matrices of the neural network describing the ways in which the data from the MOS gas sensor, microphone, and pressure sensor are likely to affect what and when physiological messages should be presented to a user.

With the output layer, the information handling system may provide data descriptive of what physiological messages should be presented to a user. The dataset related to the physiological messages that should be presented to the user may be used by the processor of the information handling system executing a biofeedback headset machine learning system to provide those messages commensurate with the game action during game play.

At block 1150, the method 1100 may include determining whether the biometric data relative to the game play data warrant a warning to be displayed to the user. Here, the biofeedback headset machine learning system may be used by the processor as described above to not only help determine whether a message should be displayed to a user, but what that message should be. For example, where the first-person shooter gaming application is being executed and the recorded data at blocks 1105-1140 have been used as input to the biofeedback headset machine learning system, the processor may receive output indicating that the user should increase a respiratory rate, decrease a respiratory rate, provide a better air quality during game play, improve room ventilation, attempt to reduce stress, or any other warning that, based on the data received at the biofeedback headset machine learning system, could help to improve the user's health during game play while also providing the best opportunity for the user to succeed in the game play.

Where a message or warning is warranted at block 1150, the method 1100 may proceed at block 1155 with providing the warning or message to the user. Where the biometric data does not indicate that a warning or message is warranted, the method may continue to monitor for such a need at block 1160 by repeating the processes found at blocks 1110-1145. The process may then end when, for example, the user disengages with the game play or the power to the information handling system is removed by the press of a power off switch.

The blocks of the flow diagrams of FIG. 11 or steps and aspects of the operation of the embodiments herein and discussed herein need not be performed in any given or specified order. It is contemplated that additional blocks, steps, or functions may be added, some blocks, steps or functions may not be performed, blocks, steps, or functions may occur contemporaneously, and blocks, steps or functions from one flow diagram may be performed within another flow diagram.

Devices, modules, resources, or programs that are in communication with one another need not be in continuous communication with each other, unless expressly specified otherwise. In addition, devices, modules, resources, or programs that are in communication with one another can communicate directly or indirectly through one or more intermediaries.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The subject matter described herein is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents and shall not be restricted or limited by the foregoing detailed description.

What is claimed is:

1. A biofeedback headset for providing input to and receiving output from an information handling system, comprising:
    a controller to send and receive audio signals to and from the information handling system and send biofeedback signals to the information handling system;
    one or more speakers mounted to a wearable head band to provide audio output from the information handling system to a user; and
    a mouthpiece operatively coupled to the wearable headband including:
        a microphone to receive audio input from the user;
        a pressure sensor to detect a breathing rate and amplitude of the user and, with the controller, provide breathing rate and amplitude biofeedback signals to the information handling system; and
        a gas sensor to detect a composition of air at the mouthpiece as the user respirates and, with the controller, provide air composition biofeedback signals to the information handling system.

2. The biofeedback headset of claim 1, further comprising a micro-fan fluidically coupled to the pressure sensor via a sensor tube to draw air into the mouthpiece at constant pressure at the pressure sensor.

3. The biofeedback headset of claim 1, further comprising a micro-fan fluidically coupled to the gas sensor via a sensor tube to pass air respirated by the user over the gas sensor.

4. The biofeedback headset of claim 1, further comprising a first earpiece on the wearable head band to house a first speaker for a first ear of the user and a second earpiece on the wearable head band to house a second speaker for a second ear of the user.

5. The biofeedback headset of claim 1, wherein the pressure sensor includes a microelectromechanical systems (MEMS) capacitive pressure sensor to detect a change in pressure above a base air pressure.

6. The biofeedback headset of claim 1, wherein the gas sensor includes a microelectromechanical systems (MEMS) metal oxide semiconductor (MOS) gas sensor that measures an amount of carbon dioxide ($CO_2$) at the mouthpiece.

7. An information handling system executing a gaming application, comprising:
    a processor executing code of the gaming application;
    a memory;
    a power source;
    a biofeedback headset including:
        a mouthpiece operatively coupled to a head band of the biofeedback headset;
        a controller to send and receive audio signals to and from the information handling system and send biofeedback signals to the information handling system from:
            a pressure sensor used detect a breathing rate and amplitude of the user via the mouthpiece; and
            a gas sensor used to detect a composition of air the user respirates via the mouthpiece, and;
    a biofeedback headset machine learning system to:
        use, as input to the processor executing code of a biofeedback headset machine learning system, the biofeedback signals from the pressure sensor and gas sensor; and
        provide, as output form the processor executing code of the biofeedback headset machine learning system, health messages to the user.

8. The information handling system of claim 7, wherein the pressure sensor includes a microelectromechanical systems (MEMS) capacitive pressure sensor to detect a change in pressure above a base air pressure.

9. The information handling system of claim 7, wherein the gas sensor includes a microelectromechanical systems (MEMS) metal oxide semiconductor (MOS) gas sensor that measures an amount of carbon dioxide ($CO_2$) at the mouthpiece.

10. The information handling system of claim 7 further comprising:
    the biofeedback headset including a first earpiece operatively coupled to the head band to house a first speaker for a first ear of the user and a second earpiece operatively coupled to the head band to house a second speaker for a second ear of the user.

11. The information handling system of claim 7 further comprising:
    a micro-fan fluidically coupled via an air tube to the gas sensor to pass air respirated by the user over the gas sensor.

12. The information handling system of claim 7 further comprising:
    a micro-fan fluidically coupled via an air tube to the pressure sensor to draw air, at a constant pressure, at the pressure sensor.

13. The information handling system of claim 7, wherein the health messages include indications to a user that the respiration of the user indicates is suboptimal and, based on the action presented to the user during the execution of the gaming application, should be regulated.

14. The information handling system of claim 7, wherein the input to the biofeedback headset machine learning system further includes game play interaction of the user during the execution of the gaming application, intensity of the game play during the execution of the gaming application, a difficulty level during the execution of the gaming application, an opponent level difficulty during the execution of the gaming application, and teamwork level during the execution of the gaming application.

15. A biofeedback headset for providing input to and receiving output from an information handling system, comprising:
    a controller to send and receive audio signals to and from the information handling system and send biofeedback signals to the information handling system;
    a wired connection to the information handling system including:
        a data line for the controller to send and receive the audio signals and send the biofeedback signals; and
        a power line to provide power to the controller;
    a mouthpiece operatively coupled to a headband of the biofeedback headset including:
        a microphone to receive audio input;
        a pressure sensor to detect a breathing rate and amplitude of the user and, with the controller, provide breathing rate and amplitude biofeedback signals to a biofeedback headset machine learning system of the information handling system;
        a gas sensor to detect a composition of air at the mouthpiece as the user respirates and, with the controller, provide air composition biofeedback signals to a biofeedback headset machine learning system of the information handling system.

16. The biofeedback headset of claim 15 further comprising:
    a micro-fan to draw air over the pressure sensor and maintain a benchmark pressure at the pressure sensor.

17. The biofeedback headset of claim 15 further comprising:
    a micro-fan to draw air over the gas sensor to detect the composition of the air respirated by the user.

18. The biofeedback headset of claim 15 further comprising:
    a rubber-sealed chamber to seal the gas sensor and pressure sensor from a microphone chamber housing the microphone.

19. The biofeedback headset of claim 15 further comprising:
    a micro-fan to draw air over the pressure sensor and gas sensor;
    an air tube fluidically coupling the micro-fan to a sensor chamber housing the gas sensor and pressure sensor; and
    a signal cable to send signals from the gas sensor and pressure sensor to the controller.

20. The biofeedback headset of claim 15 further comprising:
    a microphone tube operatively coupling the mouthpiece to a portion of a housing of the biofeedback headset to provide structural support to a microphone signal cable placed coaxially within the microphone tube and operatively coupling the microphone to the controller.

\* \* \* \* \*